US010995316B2

(12) United States Patent
Stumpe

(10) Patent No.: US 10,995,316 B2
(45) Date of Patent: May 4, 2021

(54) PROLINE AUXOTROPHS

(71) Applicant: CALYSTA, INC., Menlo Park, CA (US)

(72) Inventor: Jana Stumpe, Sunnyvale, CA (US)

(73) Assignee: CALYSTA, INC., Menlo Park, CA (US)

( * ) Notice: Subject to any disclaimer, the term of this patent is extended or adjusted under 35 U.S.C. 154(b) by 0 days.

(21) Appl. No.: 15/573,685

(22) PCT Filed: May 13, 2016

(86) PCT No.: PCT/US2016/032297
§ 371 (c)(1),
(2) Date: Nov. 13, 2017

(87) PCT Pub. No.: WO2016/183413
PCT Pub. Date: Nov. 17, 2016

(65) Prior Publication Data
US 2018/0105791 A1 Apr. 19, 2018

Related U.S. Application Data

(60) Provisional application No. 62/160,896, filed on May 13, 2015.

(51) Int. Cl.
C12N 1/20 (2006.01)
C07K 14/195 (2006.01)
C12P 7/56 (2006.01)
C12N 9/06 (2006.01)
C12N 15/74 (2006.01)
C07D 207/12 (2006.01)

(52) U.S. Cl.
CPC .............. C12N 1/20 (2013.01); C07K 14/195 (2013.01); C12N 9/0028 (2013.01); C12N 15/74 (2013.01); C12P 7/56 (2013.01); C12Y 101/01027 (2013.01); C12Y 101/01244 (2013.01); C12Y 105/01002 (2013.01); C07D 207/12 (2013.01)

(58) Field of Classification Search
None
See application file for complete search history.

(56) References Cited

U.S. PATENT DOCUMENTS

2003/0166174 A1* 9/2003 Ono ................. C12P 13/04
435/106
2005/0255568 A1* 11/2005 Bailey ................. C12N 9/0006
435/113

FOREIGN PATENT DOCUMENTS

WO 2012/064619 A1 5/2012

OTHER PUBLICATIONS

Ward et al. (2004) Genomic Insights into Methanotrophy: The Complete Genome Sequence of Methylococcus capsulatus (Bath). PLoS Biology, 2(10):e303, pp. 1616-1628 (Year: 2004).*
Q608F7 (Pyrroline-5-carboxylate reductase from Methylcoccus capsulatus, UniProt Reference Accession Sequence, priority to Oct. 31, 2006, 2 pages) (Year: 2006).*
Bertels et al. (2011) Design and Characterization of Auxotrophy-Based Amino Acid Biosensors. PLoS ONE, 7(7):e41349, pp. 1-8 (Year: 2011).*
Yomantas et al. (2010) Aromatic Amino Acid Auxotrophs Constructed by Recombinant Marker Exchange in Methylophilus methylotrophus AS1 Cells Expressing the aroP-Encoded Transporter of *Escherichia coli*. Applied and Environmental Microbiology, 76(1):75-83 (Year: 2010).*
Zhang et al. (2014) Construction of a Quadruple Auxotrophic Mutant of an Industrial Polyploid *Saccharomyces cerevisiae* Strain by Using RNA-Guided Cas9 Nuclease. Applied and Environmental Microbiology, 80(24):7694-7701 (Year: 2014).*
Zdych et al. (1995) MalY of *Escherichia coli* Is an Enzyme with the Activity of a bC-S Lyase (Cystathionase). Journal of Bacteriology, 177(17):5035-5039 (Year: 1995).*
Q608F7 (Pyrroline-5-carboxylate reductase, NCBI Reference Sequence for Methylococcus capsulatus, priority to Oct. 31, 2006, 2 pages) (Year: 2006).*
Eccleston et al. (1972) Competition among Amino Acids for Incorporation into Methylococcus capsulatus. Journal of General Microbiology, 73:303-314 (Year: 1972).*
Kelly et al. (2005) Insights into the obligate methanotroph Methylococcus capsulatus. TRENDS in Microbiology, 13(5):195-198 (Year: 2005).*
Eroshin et al. (1968) Influence of Amino Acids, Carboxylic Acids and Sugars on the Growth of Methylococcus capsulatus on Methane. Journal of Applied Bacteriology, 31:560-567 (Year: 1968).*
Belitsky et al. (2001) Multiple Genes for the Last Step of Proline Biosynthesis in Bacillus subtilis. Journal of Bacteriology, 183(14):4389-4392 (Year: 2001).*
Forlani et al. (2017) Functional Characterization of Four Putative delta1-Pyrroline-5-Carboxylate Reductases from Bacillus subtilis. Frontiers in Microbiology, 8(1442):pp. 1-13 (Year: 2017).*
Henard et al. (2019) Muconic acid production from methane using rationally-engineered methanotrophic biocatalysts. Green Chemistry, 21:6731-6737 (Year: 2019).*
Eccleston et al. (1972) Assimilation and Toxicity of Exogenous Amino Acids in the Methane-oxidizing Bacterium Methylococcus capsulatus. Journal of General Microbiology, 71:541-554 (Year: 1972).*
Knief, C. (2015) Diversity and Habitat Preferences of Cultivated and Uncultivated Aerobic Methanotrophic Bacteria Evaluated Based on pmoA as Molecular Marker. Frontiers in Microbiology, 6(1346):1-38 (Year: 2015).*
UniProt, "Aromatic amino acid transport protein AroP," Accession No. P15993 (AROP_ECOLI), May 8, 2019, URL=https://www.uniprot.org/uniprot/P15993, 10 pages.
Wyborn et al., "Purification, properties and heterologous expression of formamidase from *Methylophilus methylotrophus*," *Microbiology* 140:191-195, 1994.

(Continued)

*Primary Examiner* — Neil P Hammell
(74) *Attorney, Agent, or Firm* — Seed IP Law Group LLP

(57) ABSTRACT

The present disclosure provides compositions and methods for making and using methanotrophic proline auxotrophs.

9 Claims, 7 Drawing Sheets
Specification includes a Sequence Listing.

(56) References Cited

OTHER PUBLICATIONS

Ankri et al., "Mutations in the *Corynebacterium glutamicum* Proline Biosynthetic Pathway: a Natural Bypass of the *proA* Step," *Journal of Bacteriology* 178(15):4412-4419, 1996.
Smith et al., "Characterization of Auxotrophic Mutants of *Mycobacterium tuberculosis* and Their Potential as Vaccine Candidates," *Infection and Immunity* 69(2):1142-1150, 2001.
Ward et al., "Genomic Insights into Methanotrophy: the Complete Genome Sequence of *Methylococcus capsulatus* (Bath)," *PLoS Biology* 2(10):1616-1628, 2004.
Database UniProt, Database Accession No. Q608F7 (2 pages) (Ward et al., "Genomic Insights into Methanotrophy: The Complete Genome Sequence of *Methylococcus capsulatus* (Bath)," *PLoS Biology* 2(10):1616-1628, 2004.).
Belitsky et al., "Multiple Genes for the Last Step of Proline Biosynthesis in *Bacillus subtilis*," *Journal of Bacteriology* 183(14):4389-4392, 2001.
Eccleston et al., "Assimilation and Toxicity of Exogenous Amino Acids in the Methane-oxidizing Bacterium *Methylococcus capsulatus*," *Journal of General Microbiology* 71:541-554, 1972.
Fichman et al., "Evolution of proline biosynthesis: enzymology, bioinformatics, genetics, and transcriptional regulation," *Biol. Rev.* 90:1065-1099, 2015.
Forlani et al., "Functional Characterization of Four Putative $\delta^1$-Pyrroline-5-Carboxylate Reductases from *Bacillus subtilis*," *Frontiers in Microbiology* 8(1442):1-13, 2017.
Henard et al., "Muconic acid production from methane using rationally-engineered methanotrophic biocatalysts," *Green Chem.* 21:6731-6737, 2019.

\* cited by examiner

PROLINE AUXOTROPHS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200206.420USPC_SEQUENCE_LISTING.txt. The text file is 45.9 KB, was created on Nov. 7, 2017, and is being submitted electronically via EFS-Web.

BACKGROUND

Methylotrophic bacteria utilize carbon substrates that contain one or more carbon atoms but no carbon-carbon bonds as their sole sources of carbon and energy. These substrates include methane, methanol, and other methylated compounds. Methanotrophic bacteria are methylotrophs that can utilize methane as a sole source of carbon and energy. Methanotrophs as a group are generally not well characterized, and even with the sequencing of the genomes of some species, their metabolic processes are not well understood. For example, even though the genome of the methanotroph *Methylococcus capsulatus* has been sequenced, it does not provide a complete picture of the organism's active metabolic pathways. For example, although all the functions that should allow the microorganism to grow on sugars are encoded, it is incapable of growth on multicarbon compounds. Chistoserdova et al., *Annu. Rev. Microbiol.* 63:477-499 (2009).

Molecular biology tools, such as auxotrophic hosts, that might facilitate the genetic manipulation of such organisms are relatively sparse compared to well characterized bacteria and yeast. Auxotrophs of methylotrophic bacteria have been described in the literature, and in some instances, challenges in making the auxotrophs have been observed. Kim et al. (*Appl. Microbiol. Biotechnol.* 48:105-108 (1997)) concluded that no mutation technique had been previously described that consistently produced stable auxotrophy of the methylotroph, *Methylophilus methylotrophus*. Id. Kim et al. reported that the ineffectiveness of UV irradiation in methylotrophs had been hypothesized to involve the lack of an SOS repair system (citing Higgins et al., *Nature* 286:561-564 (1980)), and that chemical mutagens had not been effective possibly due to their inability to permeate the membrane (citing de Vries et al., *FEMS Microbiol. Rev.* 39:235-258 (1986) and Holloway et al., *Antonie van Leeuwenhoek* 53:47-53 (1987)).

Yomantas et al. experienced similar difficulties using standard molecular biology methods for generating auxotrophic mutants of *Methylophilus methylotrophus. Appl. and Environmental Microbiology*, 76(1):75-83 (January 2010). Despite applying various forms of mutagenesis using N-methyl-N'-nitrosoguanadine (MNNG), Yomantas et al. were unable to find any auxotrophs that were deficient in aromatic amino acid biosynthesis. Id. They postulated the reason for this result was the failure of the corresponding amino acids added to the medium to permeate the microorganism cytoplasmic membrane in quantities sufficient for mutant growth. Id. Yomantas et al. addressed the low membrane permeability issue by introducing an *E. coli* gene, AroP, into *M. methylotrophus* that encodes a permease that transports Phe, Tyr, and Trp across the inner membranes of *E. coli* microorganism. As a consequence, the desired auxotrophs were subsequently isolated. Based on this success, Yomantas et al. recommended the introduction of foreign amino acid transporter genes for the isolation of other desired methylotrophic auxotrophs. Id.

Though progress has been made in the development of molecular biology tools for engineering methylotrophs, more are needed in order to develop engineered methylotrophic strains suitable for commercialization of desired products.

DETAILED DESCRIPTION

Figure 1:
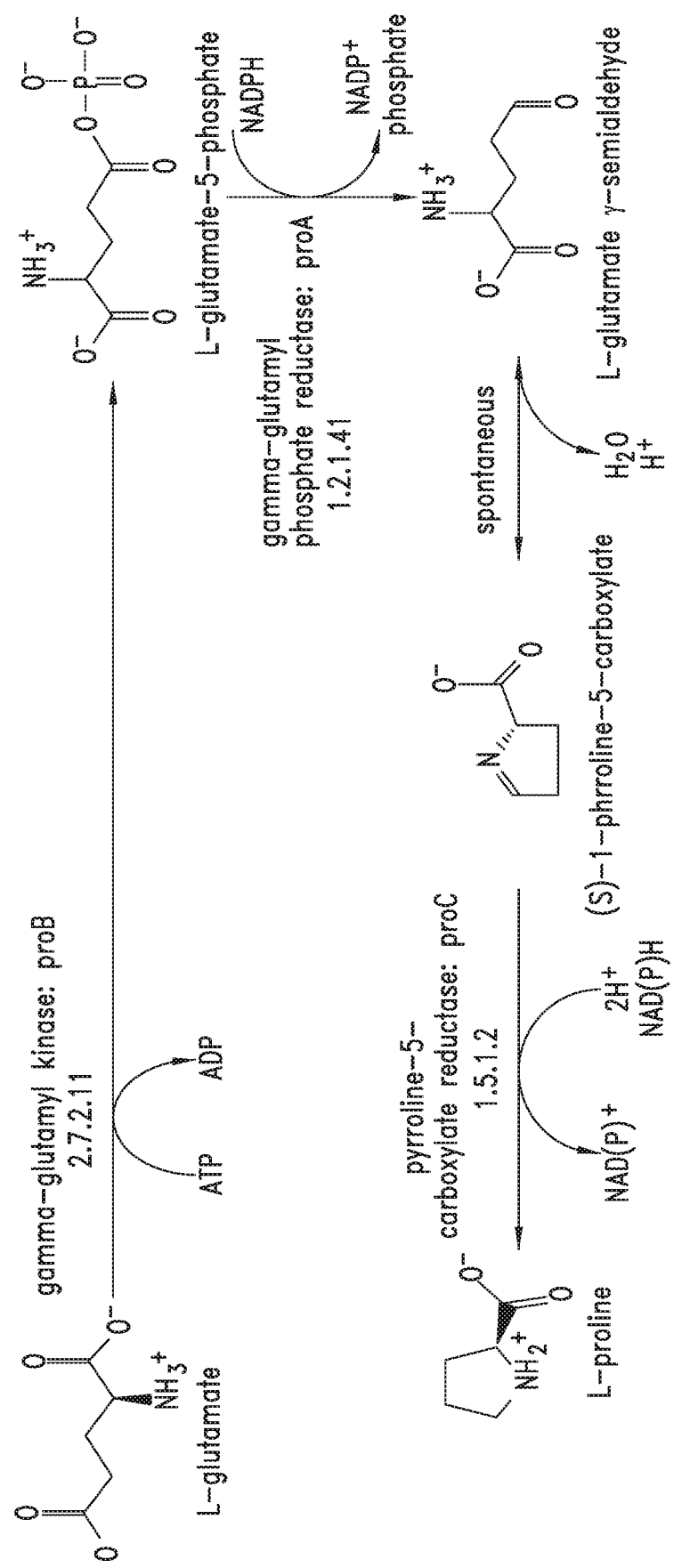
FIG. 1 depicts a proline biosynthesis pathway in *M. capsulatus* Bath strain.

The instant disclosure provides non-naturally occurring methanotrophic microorganisms that are proline auxotrophs, and related compositions and methods of making proline auxotrophic methanotrophs. The proline-responsive methanotrophic microorganisms may be used for the expression of desirable proteins where controlled cultivation on a $C_1$ substrate is desired. In certain embodiments, the proline-responsive methanotrophic microorganisms are useful for creating plasmid-addiction expression systems where antibiotic selection for maintenance of plasmid is unfeasible or undesirable.

Prior to setting forth this disclosure in more detail, it may be helpful to an understanding thereof to provide definitions of certain terms to be used herein. Additional definitions are set forth throughout this disclosure.

In the present description, the term "about" means±20% of the indicated range, value, or structure, unless otherwise indicated. The term "consisting essentially of" limits the scope of a claim to the specified materials or steps and those that do not materially affect the basic and novel characteristics of the claimed invention. It should be understood that the terms "a" and "an" as used herein refer to "one or more" of the enumerated components. The use of the alternative (e.g., "or") should be understood to mean either one, both, or any combination thereof of the alternatives. As used herein, the terms "include" and "have" are used synonymously, which terms and variants thereof are intended to be construed as non-limiting. The term "comprise" means the presence of the stated features, integers, steps, or components as referred to in the claims, but that it does not preclude the presence or addition of one or more other features, integers, steps, components, or groups thereof.

The term "methylotroph" or "methylotrophic microorganism" used herein means an organism capable of oxidizing organic compounds that do not contain carbon-carbon bonds. When the methylotroph is able to oxidize methane, the methylotroph is also a methanotroph. In certain other embodiments, the methylotrophic microorganism is an "obligate methylotrophic microorganism," which refers to methylotrophs that are limited to the use of $C_1$ substrates for the generation of energy.

The term "methanotroph" or "methanotrophic microorganism" refers to a methylotroph capable of utilizing methane as its primary source of carbon and energy. Complete oxidation of methane to carbon dioxide occurs by aerobic degradation pathways. As used herein, "methanotrophic microorganisms" include "obligate methanotrophic microorganisms" that can only utilize $C_1$ substrates (e.g., methane) for carbon and energy sources, and do not utilize organic compounds that contain carbon-carbon bonds (i.e., multi-carbon-containing compounds) as a source of carbon and energy. Also included are "facultative methanotrophic microorganisms" that are naturally able to use, in addition to $C_1$ substrates (e.g., methane), multi-carbon substrates, such as acetate, pyruvate, succinate, malate, or ethanol, as their carbon and energy source.

The term "parental" or "host" refers herein to a methanotrophic microorganism or strain that is the direct ancestor of an auxotrophic methanotroph of the present disclosure. A parental methanotrophic microorganism expresses a pyrroline-5-carboxylate reductase activity or comprises an endogenous proC gene. A parental methanotrophic microorganism may be a wild type methanotrophic microorganism, or may be an altered or mutated form of a wild type methanotrophic microorganism.

The term "auxotrophic methanotroph" refers herein to a recombinant methanotrophic microorganism that has a mutation in an endogenous gene encoding an enzyme involved in the synthesis of a specific nutrient (e.g., amino acid), whereby the mutation alters the requirements of the methanotrophic microorganism for that nutrient relative to the parental methanotrophic microorganism. In certain embodiments, the endogenous gene encoding an enzyme involved in the synthesis of a specific nutrient is knocked out or deleted in an auxotrophic methanotroph.

As used herein, the term "auxotrophic mutation" refers to a substitution, deletion, insertion or combinations thereof of one or more nucleotides in the chromosome of a parental methanotrophic microorganism, which operate singly or in concert to render the host microorganism auxotrophic with respect to a nutrient that is needed for growth (e.g., amino acid).

As used herein the terms "proline auxotroph" and "auxotrophic for proline" refer to an methanotrophic microorganism that is unable to synthesize the proline it requires for growth.

The term "proline-containing" when used in connection with a cell culture medium means a cell culture medium comprising proline. The proline may be added to the culture medium or produced by another microorganism in the same culture.

As used herein, the term "proline-free" when used in connection with a cell culture medium means a cell culture medium having no detectable proline as measured in accordance with the Quantitation of Proline assay (as described in Example 3).

As used herein, the term "proline-responsive methanotrophic expression system" refers to a methanotrophic cell that requires proline for growth, expression of a desired protein, or both.

The term "1-pyrroline-5-carboxylate reductase" or "pyrroline-5-carboxylate reductase" (also known as proline oxidase, L-proline oxidase, NADPH-L-$\delta^1$-pyrroline carboxylic acid reductase, and L-proline-NAD(P)+5-oxidoreductase) refers herein to an enzyme capable of catalyzing the reduction of 1-pyrroline-5-carboxylate to proline in accordance with the enzyme classification E.C. 1.5.1.2. Complementation of proline auxotrophs by providing a putative 1-pyrroline-5-carboxylate reductase encoding gene (e.g., proC) in trans, as described in Example 2, is used to assess whether the encoded protein exhibits 1-pyrroline-5-carboxylate reductase activity. Growth in a proline-free cell culture medium in the presence of methane is an indication that the encoded protein is a 1-pyrroline-5-carboxylate reductase or has 1-pyrroline-5-carboxylate reductase activity.

The term "$C_1$ substrate" refers herein to any carbon containing molecule that lacks a carbon-carbon bond. Examples include methane, methanol, formaldehyde, formic acid, carbon monoxide, carbon dioxide, a methylated amine (such as, for example, methyl-, dimethyl-, and trimethylamine), methylated thiols, methyl halogens (e.g., bromomethane, chloromethane, iodomethane, dichloromethane, and the like), cyanide, or the like.

As used herein, the term "culturing" or "cultivation" refers to growing a population of microbial cells under suitable conditions in a liquid or a solid medium. In some embodiments, culturing refers to fermentative bioconversion of a $C_1$ substrate to an end product.

As used herein, the term "growth phenotype" refers to the conditional response of a culture of parental methanotrophic microorganisms or auxotrophs thereof, under a particular set of environmental conditions (e.g., a defined culture medium, solid or liquid, and a particular amount of time to allow for growth), wherein (a) the number of viable microorganisms in the culture population expands or increases (i.e., grows), (b) the number of viable microorganisms in the culture population remains about the same (e.g., the cells do not divide or the relative rate of cell death to cell division is about the same (i.e., does not grow), or (c) the number of viable microorganisms in the culture population declines or decreases (i.e., does not grow).

When used in connection with describing the growth phenotype of a proline auxotroph of the present disclosure and transformants thereof, the term "no growth" refers to a growth rate (as measured by $OD_{600}$ over a defined period of time) of less than 10% in a proline-free culture medium as compared to the growth rate in the same culture medium supplemented with 100 µg/mL L-proline and for the same amount of time (see Example 2), wherein a culture is started by inoculating a defined culture medium at a starting $OD_{600}$ of 0.1 and analyzed for $OD_{600}$ after about 1 hour up to about 95 hours post-inoculation.

As used herein, the term "substantially similar growth rate" in connection with a reference cell strain refers herein to a growth rate that is at least about 75% of the reference cell strain growth rate as measured by optical density units as a function of time.

As used herein, the term "desired protein" means a protein which itself is a desired substance to be produced or which production is desired to be enhanced from a host methanotrophic microorganism, or is an enzyme that participates in concert with other enzymes in a biosynthetic metabolic pathway, the metabolic product of such pathway being a desired substance to be produced or which production is desired to be enhanced from a host methanotrophic microorganism.

The term "endogenous" or "native" refers to a referenced molecule or activity that is present in the host or parental methanotrophic microorganism.

The term "heterologous" or "foreign" refers to a molecule or activity that is derived from a source other than the referenced species or strain whereas "homologous" refers to a molecule or activity derived from the host microorganism. The term "foreign" or "heterologous" in connection with a nucleic acid or gene refers to a nucleic acid or gene that is not endogenous to the reference host microorganism. Accordingly, a microorganism comprising an exogenous nucleic acid as provided in the present disclosure can utilize either or both a heterologous or homologous nucleic acid.

As used herein, "exogenous" means that the referenced molecule (e.g., nucleic acid) or referenced activity (e.g., pyrroline-5-carboxylate reductase activity) is introduced into a host microorganism. The molecule can be introduced, for example, by introduction of a nucleic acid into the host genetic material such as by integration into a host chromosome or by introduction of a nucleic acid as non-chromosomal genetic material, such as on a plasmid. When the term is used in reference to expression of an encoding nucleic acid, it refers to introduction of the encoding nucleic acid in an expressible form into the host microorganism. When used in reference to an enzymatic or protein activity, the term refers to an activity that is introduced into the host microorganism.

It is understood that when more than one exogenous or recombinant nucleic acid is included in a bacterium or organism, the more than one exogenous or recombinant nucleic acid refers to the referenced encoding nucleic acid or enzymatic activity. It is also understood, as disclosed herein, that such more than one exogenous or recombinant nucleic acids can be introduced into the host bacterium or organism on separate nucleic acid molecules, on a polycistronic nucleic acid molecule, on a single nucleic acid molecule encoding a fusion protein, or a combination thereof, and still be considered as more than one exogenous nucleic acid. For example, as disclosed herein, an organism can be modified to express two or more exogenous nucleic acids encoding a desired pathway enzyme or protein (e.g., proline synthesis pathway enzymes). Where two exogenous or recombinant nucleic acids encoding desired proteins are introduced into a host organism, it is understood that the two exogenous or recombinant nucleic acids can be introduced as a single nucleic acid molecule, for example, on a single plasmid, on separate plasmids, can be integrated into the host chromosome at a single site or multiple sites, and still be considered two exogenous nucleic acids. Similarly, it is understood that more than two exogenous or recombinant nucleic acids can be introduced into a host organism in any desired combination, for example, on a single plasmid, on separate plasmids, can be integrated into the host chromosome at a single site or multiple sites, and still be considered as two or more exogenous or recombinant nucleic acids. Thus, the number of referenced exogenous or recombinant nucleic acids or enzymatic activities refers to the number of encoding nucleic acids or the number of enzymatic activities, not the number of separate nucleic acid molecules introduced into the host organism.

The term "introduced" in the context of inserting a nucleic acid molecule into a cell means transfected, transduced or transformed (collectively "transformed"), wherein the nucleic acid molecule is incorporated into the genome of the cell or is on an episomal plasmid that is maintained through multiple generations.

As used herein, the term "genetic modification" refers to a genetic modification of the parental methanotrophic microorganism, such as, for example, by knock out or deletion of an endogenous gene (for example, by insertion of an in-frame mutation into the gene) or introduction of a heterologous polynucleotide into the methanotrophic microorganism in a plasmid or vector or by integration into the chromosome of the methanotrophic microorganism. Genetic modifications include, for example, modifications introducing expressible nucleic acid molecules encoding proteins, other nucleic acid additions, nucleic acid deletions, nucleic acid substitutions, or other functional disruption of the microorganism's genetic material. Such modifications include, for example, coding regions and functional fragments thereof for heterologous or homologous polypeptides of the referenced species. Additional modifications include, for example, non-coding regulatory regions in which the modifications alter expression of a gene or operon. Genetic modifications to nucleic acid molecules encoding enzymes, or functional fragments thereof, can confer a biochemical reaction capability or improvements of such capabilities to the non-naturally occurring microorganism that is altered from its naturally occurring state.

As used herein, the term "non-naturally occurring", when used in reference to a microorganism, means that the microorganism has at least one genetic modification that is not normally found in a naturally occurring strain of the referenced species, including wild-type strains of the referenced species.

As used herein, the term "inactivating mutation" when used in the context of an endogenous proC gene refers to a substitution, deletion, insertion or combinations thereof of one or more nucleotides into the proC gene in the chromosome of a methanotrophic microorganism strain that results in the inability of the strain to grow in the presence of methane in a proline-free liquid culture medium.

As used herein, "nucleic acid", also known as "polynucleotide", refers to a polymeric compound comprised of covalently linked subunits called nucleotides. Nucleic acids include polyribonucleic acid (RNA), polydeoxyribonucleic acid (DNA), either of which may be single or double stranded. DNA includes cDNA, genomic DNA, synthetic DNA, and semi-synthetic DNA.

As used herein, the term "coding sequence" is intended to refer to a polynucleotide molecule, which encodes the amino acid sequence of a protein product. The boundaries of the coding sequence are generally determined by an open reading frame, which usually begins with an ATG start codon.

The term "nucleic acid construct" refers herein to a nucleic acid molecule, either single- or double-stranded, which is isolated from a naturally occurring source or which has been modified to contain segments of nucleic acids in a manner that would not otherwise exist in nature. The term "nucleic acid construct" is synonymous with the term "expression cassette" when the nucleic acid construct contains the control sequences required for expression of a recombinant polynucleotide encoding a desired protein.

The term "control sequences" refers herein to all the components that are necessary or advantageous for the expression of a desired protein in a host cell. Each control sequence may be native or foreign to the nucleotide sequence encoding the desired protein. Such control sequences can include a leader, a promoter (e.g., native, exogenous or chimeric), a signal peptide sequence, a transcription terminator, or the like. At a minimum, a control sequence includes a promoter along with transcriptional and translational stop signals. The control sequences may be provided with linkers for the purpose of introducing specific restriction sites facilitating ligation of the control sequences with the coding region of the nucleotide sequence encoding a polypeptide.

The term "expression" as used herein refers to any step involved in the production of the polypeptide, including transcription, post-transcriptional modification, translation, post-translational modification, secretion or the like.

The term "expression vector" refers herein to a DNA molecule, linear or circular, that comprises a segment corresponding to the first and/or second recombinant polynucleotide described herein, which is operably linked to additional segments that provide for its transcription.

The term "operably linked" refers herein to a configuration in which a control sequence is appropriately placed at a position relative to the coding sequence of the DNA sequence such that the control sequence influences the expression of a polypeptide.

The terms "percent identity", "% identity", "percent identical", and "% identical" are used interchangeably herein to refer the percent amino acid sequence identity that is obtained by ClustalW analysis (version W 1.8 available from European Bioinformatics Institute, Cambridge, UK), counting the number of identical matches in the alignment and dividing such number of identical matches by the length of the reference sequence, and using the following default ClustalW parameters to achieve slow/accurate pairwise optimal alignments—Gap Open Penalty: 10; Gap Extension Penalty: 0.10; Protein weight matrix: Gonnet series; DNA weight matrix: IUB; Toggle Slow/Fast pairwise alignments=SLOW or FULL Alignment.

As used herein, the term "plasmid-addicted methanotrophic expression system" refers to a proline auxotroph of the present disclosure that further comprises a nucleic acid construct that is capable of complementing the proline deficiency of the auxotroph.

The term "recombinant" when used in connection with a polynucleotide, polypeptide, or cell when it is artificial or engineered. For example, a polynucleotide that is inserted into a vector or any other heterologous location, e.g., in a genome of a recombinant organism, such that it is not associated with nucleotide sequence that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example, a variant of a naturally occurring gene, is recombinant.

As used herein, the term "transformed" or "transformation" used in reference to a cell means a cell has a non-native nucleic acid sequence integrated into its genome or as an episomal plasmid that is maintained through multiple generations.

The term "variant" refers herein to a polypeptide which differs in one or more amino acid position(s) from that of a parent polypeptide sequence (e.g., by substitution, deletion, insertion or combinations thereof).

The term "wild type" as applied to a microorganism (strain), polypeptide or polynucleotide means a microorganism (strain), polypeptide, or polynucleotide found in nature.

Proline Auxotrophs and Expression Systems

The present disclosure provides mutant methanotrophic microorganisms that are proline auxotrophs. Proline auxotrophs of the present disclosure are also useful for generating desired non-natural or recombinant microorganisms, or as methanotrophic expression systems for producing desired recombinant proteins. Non-naturally occurring proline auxotrophs of the present disclosure are prepared by altering (e.g., mutating, inactivating, deleting) a nucleic acid molecule encoding a pyrroline-5-carboxylate reductase activity (e.g., proC) in a desired host (parental) methanotrophic microorganism. A methanotrophic microorganism that is to be genetically modified may be a natural strain, strain adapted (e.g., performing fermentation to select for strains with improved growth rates or increased total biomass yield compared to the parent strain), or previously recombinantly modified to utilize multi-carbon substrates, to have increased growth rates, or any combination thereof.

In certain aspects, the present disclosure provides a non-naturally occurring proline auxotroph, wherein the proline auxotroph is a methanotrophic microorganism comprising an altered endogenous nucleic acid encoding a pyrroline-5-carboxylate reductase, wherein the proline auxotroph exhibits a growth phenotype of no growth when cultured in a proline-free culture medium and in the presence of a $C_1$ substrate (e.g., methane, methanol). Exemplary alterations or mutations include a substitution, deletion, insertion or combinations thereof of one or more nucleotides in a proC gene in the chromosome of a methanotrophic microorganism. In some embodiments, the $C_1$ substrate is methane, natural gas or methanol.

In certain other embodiments, the altered endogenous nucleic acid comprises an addition or deletion mutation of an endogenous chromosomal proC gene (a deletion mutant is also referred to as ΔproC), wherein pyrroline-5-carboxylate reductase activity is eliminated or minimized. For example, a chromosomal mutation comprises a deletion of all or a portion of an endogenouse proC gene, wherein the deletion results in either no product being produced or a polypeptide lacking pyrroline-5-carboxylate reductase activity (e.g., a truncated pyrroline-5-carboxylate reductase). In still other embodiments, the altered endogenous nucleic acid comprises an inactivating substitution mutation (e.g., transition, transversion, nonsense, missense) in an endogenous chromosomal proC gene, wherein the encoded polypeptide lacks or has minimal pyrroline-5-carboxylate reductase activity.

In certain embodiments, a proline auxotroph is a proC deletion mutant (ΔproC) of a parental methanotrophic microorganism, in which the DNA corresponding to all or a functional portion of the endogenous proC has been removed from the chromosome of a parental methanotrophic microorganism. ProC encodes a pyrroline-5-carboxylate reductase, which catalyzes the reduction of 1-pyrroline-5-carboxylate to proline with a concomitant oxidation of NAD(P)H to NAD(P)$^+$. An illustrative proline biosynthesis pathway in a methanotroph (*M. capsulatus* Bath strain) is illustrated in FIG. 1. Methods for making proline auxotrophs of the present disclosure are described in more detail herein.

In certain embodiments, the present disclosure provides a non-naturally occurring proline auxotroph, wherein the proline auxotroph is a methanotrophic microorganism that is a mutant of a parental methanotrophic microorganism, wherein relative to the parental methanotrophic microorganism, the proline auxotroph has a chromosomal mutation comprising a deletion of an endogenous proC gene (ΔproC) or comprising an inactivating mutation of an endogenous proC gene, and wherein the proline auxotroph cultured in the presence of methane exhibits a growth phenotype of (a) no growth when cultured in a proline-free culture medium, and (b) growth when cultured in a proline-containing culture medium.

Proline auxotrophs of the present disclosure are capable of growing at relatively low concentrations of proline. In certain embodiments, a culture medium will contain proline at a concentration of at least about 10 μg/mL, and in some instances at least about 15 μg/mL, at least about 20 μg/mL, at least about 25 μg/mL, at least about 30 μg/mL, at least about 35 μg/mL, at least about 40 μg/mL, at least about 45 μg/mL, at least about 50 μg/mL, at least about 55 μg/mL, 60 μg/mL, 65 μg/mL, 70 μg/mL, 75 μg/mL, 80 μg/mL, 85 μg/mL, 90 μg/mL, 95 μg/mL, or at least about 100 μg/mL or more. In certain other embodiments, the concentration of proline in a culture medium is at least about 20 μg/mL and not more than about 500 μg/ml, 450 μg/ml, 400 μg/ml, 350 μg/ml, 300 μg/ml, 250 μg/ml, about 200 μg/mL, or about 150 μg/mL. In further embodiments, the concentration of proline in a culture medium ranges from about about 25 μg/mL to about 500 μg/mL, about 25 μg/mL to about 250 μg/mL, about 50 μg/mL to about 250 μg/mL, about 75 μg/mL to about 250 μg/mL, or about 100 μg/mL to about 250 μg/mL. In other embodiments, the concentration of proline in a culture medium ranges from about 25 μg/mL to about 200 μg/mL, about 50 μg/mL to about 200 μg/mL, about 75 μg/mL to about 200 μg/mL, or about 100 μg/mL to about 200 μg/mL. In still other embodiments, the concentration of proline in a culture medium ranges from about 25 μg/mL to about 150 μg/mL, or about 50 μg/mL to about 100 μg/mL.

When cultured in the presence of methane, proline auxotrophs of the present disclosure grow when complemented with proline either via a proline-containing culture medium or via a plasmid comprising a gene that complements the proline deficiency. The proline auxotrophs do not grow in the absence of proline. In contrast to the aromatic amino acid auxotrophs of *Methylophilus methylotrophus* described by Yomantas et al., when the proline auxotrophs of the present disclosure are cultured in the presence of methane and when they do not further comprise any heterologous amino acid transporter genes, they exhibit the growth phenotype of: (a) no growth when cultured in a proline-free culture medium; and (b) growth when cultured in a proline-containing culture medium. Cf. Yomantas et al., *Appl. Environ. Microbiol.* 76(1):75-83 (2010). Thus, proline auxotrophs of the present disclosure surprisingly do not require a recombinant amino acid transporter gene to facilitate the transport of amino acid (e.g., proline) across the cytoplasmic membrane. In certain embodiments, proline auxotrophs do not further comprise a recombinant polynucleotide encoding a proline transporter.

In other embodiments, a non-natural proline auxotroph further comprises a recombinant polynucleotide encoding a proline transporter. In certain embodiments, a proline transporter may be a Na$^+$/L-proline transporter PutP, which catalyzes the uptake of extracelluar L-proline. Examples of PutP amino acid sequences that may be encoded by recombinant polynucleotides include NP_415535 (*E. coli* strain K-12), NP_249474 (*Pseudomonas aeruginosa*), NP_845968 (*Bacillus anthracis*), YP_500611 (*Staphylococcus aureus*), and NP_455619 (*Salmonella typhii*).

In certain embodiments, a proline auxotroph (and corresponding parental microorganism) is a methanotroph or a methylotroph. Exemplary methanotrophs include a *Methylomonas* sp., a *Methylobacter* sp., a *Methylococcus* sp., a *Methylosinus* sp., a *Methylocystis* sp., a *Methylomicrobium* sp., a *Methanomonas* sp., a *Methylocella* sp., or the like. Representative methylotroph species include *Methylobacterium extorquens*, *Methylobacterium radiotolerans*, *Methylobacterium populi*, *Methylobacterium chloromethanicum*, *Methylobacterium nodulans*, or a combination thereof.

In certain embodiments, methanotrophic microorganisms are altered to be proline auxotrophs that are capable of converting C$_1$ substrates into desired products. Methanotrophic microorganisms have the ability to oxidize methane as a carbon and energy source. Methanotrophic microorganisms are classified into three groups based on their carbon assimilation pathways and internal membrane structure: type I (gamma proteobacteria), type II (alpha proteobacteria, and type X (gamma proteobacteria). Type I methanotrophs use the ribulose monophosphate (RuMP) pathway for carbon assimilation whereas type II methanotrophs use the serine pathway. Type X methanotrophs use the RuMP pathway but also express low levels of enzymes of the serine pathway. Methanotrophic microorganisms include obligate methanotrophs, which can only utilize C$_1$ substrates for carbon and energy sources, and facultative methanotrophs, which naturally have the ability to utilize some multi-carbon substrates as a sole carbon and energy source.

Exemplary facultative methanotrophs include some species of *Methylocella*, *Methylocystis*, and *Methylocapsa* (e.g., *Methylocella silvestris*, *Methylocella palustris*, *Methylocella tundrae*, *Methylocystis daltona* strain SB2, *Methylocystis bryophila*, and *Methylocapsa aurea* KYG), *Methylobacterium organophilum* (ATCC 27,886), *Methylibium petroleiphilum*, or high growth variants thereof. In certain embodiments, a proline auxotroph (and corresponding parental microorganism) is a facultative methanotrophic microorganism, such as, for example, a *Methylocella* sp., a *Methylocystis* sp., a *Methylocapsa* sp., or the like. Illustrative species include, for example, *Methylobacterium extorquens* AM1, *Methylobacterium nodulans*, *Methylobacterium populi*, *Methylobacterium chloromethanicum*, *Methylobacterium extorquens*, *Methylocella silvestris*, *Methylocella palustris*, *Methylocella tundrae*, *Methylocystis daltona* strain SB2, *Methylocystis bryophila*, *Methylocapsa aurea* KYG, *Methylobacterium organophilum* (ATCC 27,886), *Methylibium petroleiphilum*, or the like.

Exemplary obligate methanotrophic microorganisms include *Methylococcus capsulatus* Bath, *Methylomonas* 16a (ATCC PTA 2402), *Methylosinus trichosporium* OB3b (NRRL B-11,196), *Methylosinus sporium* (NRRL B-11, 197), *Methylocystis parvus* (NRRL B-11,198), *Methylomonas methanica* (NRRL B-11,199), *Methylomonas albus*

(NRRL B-11,200), *Methylobacter capsulatus* (NRRL B-11, 201), *Methylomonas flagellata* sp AJ-3670 (FERM P-2400), *Methylacidiphilum infernorum, Methylacidiphilum fumariolicum, Methylomicrobium alcaliphilum*, or high growth variants thereof. In certain embodiments, a proline auxotroph is an obligate methanotrophs, such as *Methylococcus capsulatus* Bath or *Methylomonas* 16a (ATCC PTA 2402).

In certain embodiments, a proline auxotroph is an obligate methylotroph. Illustrative genera of obligate methylotrophs includes *Methylophilus* sp., *Methylobacillus* sp., *Methylovorus* sp., and *Methylophaga* sp.

The methanotrophic microorganism employed in the practice of the present disclosure may be either an aerobic methanotrophic microorganism or an anaerobic methanotrophic microoganism. In certain embodiments, a methonotrophic microorganism employed in the practice of the present disclosure is an aerobic methanotrophic microorganism.

The endogenous proC gene targeted for mutation can be identified from genomic sequences of methanotrophs in databases such as, for example, the integrated microbial genomes (IMG) system provided by the Joint Genome Institute (img.jgi.doe.gov), or in accordance with a sequence homology search using one or more of the amino acid sequences for 1-pyrroline-5-carboxylase set forth in Table 1 as reference sequences. Table 1 provides the sequences and chromosomal locus for proC genes in certain illustrative parental methanotrophic microorganisms, which can be targeted for alteration (e.g., deletion, addition or positioning of one or more inactivating mutations). The chromosomal mutation(s) can be generated using any suitable method known in the art. For example, gene deletion, gene knock out or gene mutation can be accomplished by isolating or synthesizing all or a portion of the proC gene or open reading frame thereof, and replacing, mutating, substituting, or deleting all (i.e., a gene deletion) or a portion of the proC gene to disrupt the promoter and/or open reading frame of the proC gene, and integrating the disrupted molecule, via single- or double-crossover homologous recombination events, into the genome of the methanotroph of interest. Homologous recombination may be promoted by allelic exchange using suicide vectors, as described for use with slow growing $C_1$ metabolizing microorganism by, for example, Toyama and Lidstrom, *Microbiol.* 144:183, 1998; Stolyar et al., *Microbiol.* 145:1235, 1999; Ali et al., *Microbiol.* 152:2931, 2006; Van Dien et al., *Microbiol.* 149:601, 2003.

TABLE 1

Illustrative Genomic proC Nucleic Acid Molecules

| Methanotroph | SEQ ID NO. (Native proC) | Genomic DNA Accession No. | Gemone Locus of proC (inclusive) | proC Gene Locus Tag |
| --- | --- | --- | --- | --- |
| *Methylococcus capsulatus* Bath | 1 | AE017282.2 | 1636457 to 1637281 | MCA1535 |
| *Methylomonas methanica* MC09 | 3 | CP002738.1 | 3667173 to 3668000 | Metme_3329 |
| *Methylomicrobium album* BG8 | 5 | CM001475.1 | 1528504 to 1529331 | Metal_1372 |
| *Methylomicrobium alcaliphilum* | 7 | FO082060.1 | 153346 to 154173 | MEALZ_0136 |
| *Methylobacterium extorquens* PA1 | 9 | CP000908.1 | 4181132 to 4181965 | Mext_3769 |
| *Methylobacterium extorquens* CM4 | 11 | CP001298.1 | 4284809 to 4285642 | Mchl_4063 |
| *Methylobacterium* sp. 4-46 | 13 | CP000943.1 | 992395 to 993228 | M446_0881 |
| *Methylobacterium populi* BJ001 | 15 | CP001029.1 | 4299665 to 4300495 | Mpop_4024 |
| *Methylobacterium radiotolerans* JCM 2831 | 17 | CP001001.1 | 5266117 to 5266950 | Mrad2831_4946 |
| *Methylocystis* sp. SC2 | 19 | HE956757.1 | 230498 to 231316 | BN69_0185 |
| *Methylocella silvestris* BL2 | 21 | CP001280.1 | 1224723 to 1225544 | Msil_1138 |
| *Methylobacterium nodulans* ORS 2060 | 23 | CP001349.1 | 1447053 to 1447871 | Mnod_1362 |
| *Methylibium petroleiphilum* PM1 | 25 | CP000555.1 | 3966268 to 3967089 | Mpe_A3746 |

Clones that grow in a proline-containing culture medium and do not grow in proline-free culture medium indicate the altered methanotroph has a proline auxotrophic growth phenotype. In contrast, colonies that grow in either a proline-containing culture medium or a proline-free culture medium are likely to be parental methanotrophic microorganisms (i.e., untransformed microorganisms) or other mutants that do not have the proline auxotrophic growth phenotype. Construction and selection of a ΔproC *Methylococcus capsulatus* Bath is described in Example 1.

The auxotrophs of the present disclosure may be further altered or mutated to impart or exhibit other desired phenotypes. For example, the auxotrophs may be engineered to express or overexpress an endogenous or exogenous desired protein or to attenuate expression of an undesired endogenous protein. These embodiments are described in further detail herein.

In further aspects, the present disclosure provides proline auxotrophs that are useful as proline-responsive methanotrophic expression systems for the expression of desirable proteins, such as when controlled cultivation on a $C_1$ substrate is desired. In certain embodiments, the present disclosure provides a proline-responsive methanotrophic expression system comprising a non-naturally occurring proline auxotrophic methanotroph described herein, wherein the auxotroph further comprises at least one recombinant polynucleotide that encodes a desired protein, modifies expression of an endogenous protein, or both. In some embodiments, a recombinant polynucleotide encoding a desirable protein is integrated into the auxotroph chromosome or is on a self-replicating nucleic acid construct (e.g., plasmid) containing the recombinant polynucleotide. In particular embodiments, a recombinant polynucleotide encoding a desired protein is operably linked to a promoter. A recombinant polynucleotide that modifies expression of an endogenous protein may correspond to a regulatory element that controls expression of the endogenous protein, or it may encode a metabolic pathway enzyme whose expression results in the attenuation of expression of the endogenous protein, or the like.

Figure 2:
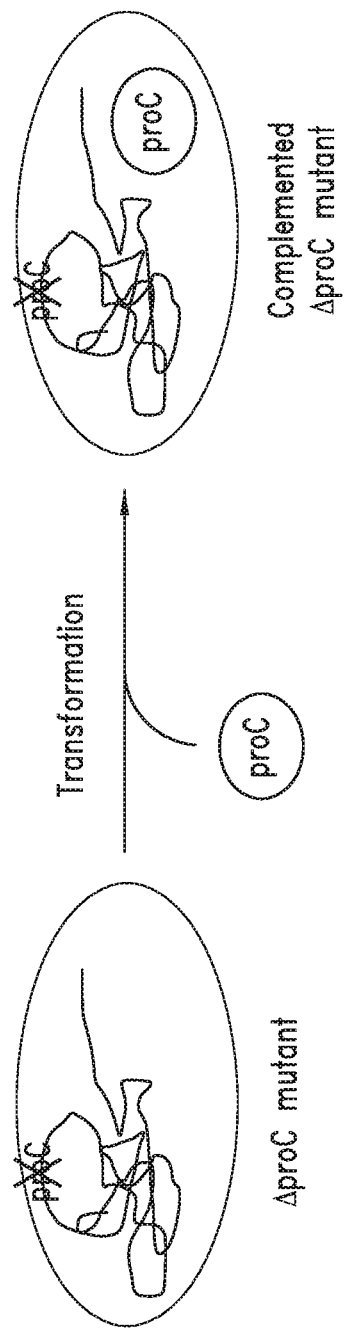
FIG. 2 depicts a kanamycin-free proline-based addiction plasmid system in a methanotrophic microorganism.

In yet other aspects, the present disclosure provides a plasmid-addicted methanotrophic expression system comprising a proline auxotroph of any of the embodiments described herein, wherein the proline auxotroph is transformed with a nucleic acid construct comprising: (1) a first recombinant polynucleotide that encodes a desired protein; and (2) a second recombinant polynucleotide that encodes 1-pyrroline-5-carboxylate reductase, and wherein the plasmid-addicted methanotrophic expression system exhibits a growth phenotype of growth when cultured in the presence of a $C_1$ substrate (e.g., methane) in a proline-free culture medium. In certain embodiments, the $C_1$ substrate is methane or methanol. The foregoing expression system is useful for, for example, preventing plasmid loss through cycles of cell division during cultivation. Plasmid loss decreases production of a desired protein and overall profitability. Use of antibiotic selection (e.g., kanamycin) may not be an applicable option to maintain plasmid stability for large scale fermentation systems due to the high costs and ecological constraints. Other factors that may be considered are the antibiotic stability at culture temperatures (e.g., 42° C.), the ATP requirements for antibiotic resistance, and the need for inactivation and removal of antibiotics from the desired product. Moreover, plasmid instability may occur even in the presence of antibiotic selection during culture (see, e.g., Zabriskie and Arcuri, *Enzyme Microb. Technol.* 8:706-717, 1985). The anabolism-based plasmid addiction system of the present disclosure is based upon the presence of an essential gene in the proline biosynthesis pathway (e.g., proC) that is missing or inactive in the host cell. If the endogenous proC is inactivated or deleted and a replacement copy of a functional gene is localized on a plasmid or on the chromosome, production of a desired protein will occur in the presence of the replacement copy of the functional gene (see FIG. 2, an example of a plasmid containing a functional gene replacement).

In any of the aforementioned aspects, embodiments of an encoded desired protein may be an enzyme, a fluorescent protein (e.g., green fluorescent protein, or the like), a therapeutic protein (e.g., ligand, receptor), a vaccine antigen, an anti-parasitic protein, or the like. In some embodiments, an encoded desired protein is a metabolic pathway enzyme involved in the biosynthesis of a metabolite (e.g., amino acid). As used herein, metabolites refer to intermediates and products of metabolism, including primary metabolites (compound directly involved in normal growth, development, and reproduction of an organism or cell) and secondary metabolites (organic compounds not directly involved in normal growth, development, or reproduction of an organism or cell but have important ecological function). Examples of metabolites that may be produced in the methanotrophic auxotrophs described herein include alcohols, amino acids, nucleotides, antioxidants, organic acids, polyols, antibiotics, pigments, sugars, vitamins or any combination thereof. Host cells containing such recombinant polynucleotides are useful for the production of desired products (e.g., lactate, isoprene, propylene), as described herein.

In some examples, a recombinant polynucleotide encoding a desired protein is a recombinant polynucleotide encoding lactate dehydrogenase (LDH). Methanotrophic microorganisms that are recombinantly modified to express or over-express a lactate dehydrogenase and are capable of converting carbon feedstock (e.g., methane) into lactate have been described in PCT Publication No. WO 2014/205145, which recombinant polynucleotides and constructs thereof are incorporated herein by reference in their entirety.

In other examples, a recombinant polynucleotide encoding a desired protein is a recombinant polynucleotide encoding a propylene synthesis pathway enzyme, for example, crotonase, crotonyl CoA thioesterase, 4-oxalocrotonate decarboxylase, or any combination thereof. Methanotrophic microorganisms that are recombinantly modified to be capable of converting carbon feedstock into propylene have been described in PCT Publication No. WO 2014/047209, which recombinant polynucleotides and constructs thereof are incorporated herein by reference in their entirety.

In still other examples, a recombinant polynucleotide encoding a desired protein is a recombinant polynucleotide encoding an isoprene synthesis pathway enzyme (e.g., isoprene synthase (IspS)). Methanotrophic microorganisms that are recombinantly modified to express or over-express isoprene synthase and are capable of converting carbon feedstock into isoprene have been described in PCT Publication No. WO 2014/138419, which recombinant polynucleotides and constructs thereof are incorporated herein by reference in their entirety.

In more examples, a recombinant polynucleotide encoding a desired protein is a recombinant polynucleotide encoding a fatty acid converting enzyme, for example a fatty acyl-CoA reductase, a fatty alcohol forming acyl-ACP reductase, a carboxylic acid reductase, or any combination thereof. Methanotrophic microorganisms that are recombinantly modified to express or over-express fatty alcohols, hydroxyl fatty acids, or dicarboxylic acids from carbon feedstock have been described in PCT Publication No. WO 2014/074886, which recombinant polynucleotides and constructs thereof are incorporated herein by reference in their entirety.

In yet more examples, a recombinant polynucleotide encoding a desired protein is a recombinant polynucleotide encoding a fatty acid elongation pathway enzyme, for example, a β-ketoacyl-CoA synthase, a β-ketoacy-CoA reductase, a β-hydroxy acyl-CoA dehydratase, an enoyl-CoA reductase, or any combination thereof. Methanotrophic microorganisms that are recombinantly modified to express or over-express very long chain fatty acids, very long chain fatty alcohols, very long chain ketones, very long chain fatty ester waxes, and very long chain alkanes have been described in U.S. Provisional Application No. 61/994,042, filed on May 15, 2014, which recombinant polynucleotides and constructs thereof are incorporated herein by reference in their entirety.

In further examples, a recombinant polynucleotide encoding a desired protein is a recombinant polynucleotide encoding an amino acid biosynthesis enzyme. For example, a lysine biosynthesis enzyme may be a lysine-sensitive aspartokinase III (lysC), an aspartate kinase, an aspartate-semialdehyde dehydrogenase (asd), a dihydrodipicolinate synthase (dapA), a dihydrodipicolinate reductase (dapB), a 2,3,4,5-tetrahydropyridine-2,6-carboxylate N-succinyltransferase (dapD), an acetylornithine/succinyldiaminopimelateaminotransferase (argD), a succinyldiaminopimelate desuccinylase (dapE), a succinyldiaminopimelate transaminase, a diaminopimelate epimerase (dapF), a diaminopimelate dicarboxylase (lysA), or the like. Exemplary tryptophan biosynthesis enzymes include a chorismate-pyruvate lyase (ubiC), an anthranilate synthase component I (trpE), an anthranilate synthase component II (trpG), an anthranilate phosphoribosyltransferase (trpD), a phosphoribosylanthranilate isomerase (trpC), a tryptophan biosynthesis protein (trpC), an N-(5'phosphoribosyl) anthranilate isomerase (trpF), an indole-3-glycerol phosphate synthase, a tryptophan synthase alpha chain (trpA), a tryptophan synthase beta chain (trpB), or the like. Representative methionine biosynthesis enzyme include a homoserine O-succinyltransferase (metA), a cystathionine gamma-synthase (metB), a protein MalY, a cystathionine beta-lyase (metC), a B12-dependent methionine synthase (metH), a 5-methyltetrahydropteroyltriglutamate-homocysteine S-methyltransferase (metE), or the like. Exemplary cysteine biosynthesis enzymes include a serine acetyltransferase (CysE), a cysteine synthase A, a cysteine synthase B, or the like. Representative threonine biosynthesis enzymes include an aspartate transaminase, a PLP-dependent aminotransferase, an aspartate aminotransferase, an aspartate kinase, an aspartate-semialdehyde dehydrogenase, a homoserine dehydrogenase, a homoserine kinase, a threonine synthase, or the like. Methanotrophic microorganisms that are recombinantly modified to express or over-express amino acids have been described in International Patent Application No. PCT/US2105/011872, filed on Jan. 16, 2015, which recombinant polynucleotides and constructs thereof are incorporated herein by reference in their entirety.

In further examples, a recombinant polynucleotide encoding a desired protein is a recombinant polynucleotide encoding a carbohydrate biosynthesis enzyme, such as, for example, pyruvate carboxylase, a phosphoenolpyruvate carboxykinase, an enolase, a phosphoglycerate mutase, a phosphoglycerate kinase, a glyceraldehyde-3-phosphate dehydrogenase, a Type A aldolase, a fructose 1,6-bisphosphatase, a phosphofructokinase, a phosphoglucose isomerase, a hexokinase, a glucose-6-phosphate, glucose-1-phosphate adenyltransferase, a glycogen synthase, glucan synthase (e.g., a β-1,3-glucan synthase), or the like. Methanotrophic microorganisms that are recombinantly modified to express or over-express carbohydrates have been described in International Patent Application No. PCT/US2105/011860, filed on Jan. 16, 2015, which recombinant polynucleotides and constructs thereof are incorporated herein by reference in their entirety.

In certain embodiments, an encoded pyrroline-5-carboxylate reductase may correspond to a naturally occurring or non-naturally occurring 1-pyrroline-5-carboxylate reductase. The naturally occurring pyrroline-5-carboxylate reductase may be endogenous (i.e., native) to the parental methanotrophic microorganism host, or it may be heterologous (i.e., non-native) to the parental methanotrophic microorganism host. Non-naturally occurring genes encoding 1-pyrroline-5-carboxylate reductase includes "nucleic acid variants," which refer to nucleic acids that may contain one or more substitutions, additions, deletions, insertions or combinations thereof, or may comprise fragment(s) of a reference nucleic acid. A reference nucleic acid refers to a selected wild-type (parent nucleic acid) encoding a 1-pyrroline-5-carboxylate reductase. Due to redundancy in the genetic code, nucleic acid variants may or may not affect amino acid sequence. When a recombinant polynucleotide encodes a pyrroline-5-carboxylate reductase that is not native to the parental methanotrophic microorganism, the polynucleotide sequence may be codon optimized to reflect the typical codon usage of the host microorganism without altering the polypeptide or polypeptide function encoded by the polynucleotide molecule. Codon optimization methods for maximal nucleic acid expression in a heterologous host have been previously described (see, e.g., Welch et al., *PLoS One* 4:e7002, 2009; Gustafsson et al., *Trends Biotechnol.* 22:346, 2004; Wu et al., *Nucl. Acids Res.* 35:D76, 2007; Villalobos et al., *BMC Bioinformatics* 7:285, 2006; U.S. Patent Publication Nos. US 2011/0111413 and US 2008/0292918; the methods of which are incorporated herein by reference in their entirety. A nucleic acid construct may contain multiple copies of the either the same or different pyrroline-5-carboxylate reductase-encoding polynucleotides, each of which encodes either the same or a different pyrroline-5-carboxylate reductase.

Polynucleotides encoding pyrroline-5-carboxylate reductase suitable for use in the compositions and methods of the present disclosure include those that encode a pyrroline-5-carboxylate reductase from a bacteria, yeast, fungi, plant, insect, or mammal, or variants thereof. With the complete genome sequence available for hundreds of organisms, the identification of nucleic acids encoding pyrroline-5-carboxylate reductase in related or distant species, including for example, homologs, orthologs, paralogs, etc., is well known in the art. These may be codon optimized for maximal expression in a desired methanotrophic microorganism using known methods. Assays for determining pyrroline-5-carboxylate reductase activity are known in the art (see, e.g., Phang et al., *Analytical Biochem.* 55:266-271 (1973); Smith et al., *Proc. Nat'l Acad. Sci. USA* 77:5221-5225 (1980); and U.S. Pat. No. 6,100,075).

Illustrative pyrroline-5-carboxylate reductase-encoding recombinant polynucleotides include those that have been codon optimized for expression in a parental methanotrophic microorganism and encode any one of the amino acid sequences corresponding to SEQ ID NOS.:2, 4, 6, 8, 10, 12, 14, 16, 18, 20, 22, 24, 26, or sequence and truncation variants thereof having functional activity. Variants of pyrroline-5-carboxylate reductase may exhibit improved solubility, expression, stability, catalytic activity, turnover rate or any combination thereof, or may be conservatively modified variants of known pyrroline-5-carboxylate reductases or of the pyrroline-5-carboxylate reductases described herein.

In any of the foregoing embodiments, a second recombinant polynucleotide encodes an amino acid sequence having at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% sequence identity with a pyrroline-5-carboxylate reductase reference sequence corresponding to any one of the amino acid sequences corresponding to SEQ ID NOS.:2, 4, 6, 8, 10, 12, 14, 16, 18, 20, 22, 24, and 26.

Recombinant pyrroline-5-carboxylate reductase-encoding polynucleotides suitable for use in the practice of the present disclosure can correspond in sequence to a deleted proC found in the parental methanotrophic microorganism, or may encode a heterologous pyrroline-5-carboxylate reductase encoded by a polynucleotide sequence that has been codon optimized for expression by the host methanotrophic microorganism. Illustrative polynucleotides encoding a pyrroline-5-carboxylate reductase correspond in sequence to any one of SEQ ID NOS.:1, 3, 5, 7, 9, 11, 13, 15, 17, 19, 21, 23, 25, or the like. In certain embodiments, a second recombinant polynucleotide has at least about 50%, at least about 55%, at least about 60%, at least about 65%, at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% sequence identity with a pyrroline-5-carboxylate reductase polynucleotide sequence corresponding to any one of SEQ ID NOS.:1, 3, 5, 7, 9, 11, 13, 15, 17, 19, 21, 23, and 25.

The first and second recombinant polynucleotides may be operably linked to the same or different promoters. Promoters and other regulatory elements that are suitable for use in the compositions and methods of this disclosure are described herein.

Nucleic Acid Constructs and Regulatory Elements

The present disclosure utilizes recombinant nucleic acid constructs comprising a recombinant polynucleotide that encodes a desired protein. Nucleic acid constructs employed in the practice of the present disclosure comprise a vector, such as, for example, a plasmid, a cosmid, a phage, a virus, a microorganism artificial chromosome (BAC), a yeast artificial chromosome (YAC), and the like, into which the first and/or second recombinant polynucleotide has been inserted, in a forward or a reverse orientation. The construct may further comprise regulatory sequences, including, for example, a promoter, operably linked to the sequences. Large numbers of suitable vectors and promoters are known to those of skill in the art, and are commercially available.

The recombinant polynucleotides described herein can be incorporated into any one of a variety of expression vectors suitable for expressing a polypeptide. Any vector that transduces genetic material into a cell, and which is replicable and viable in the relevant host can be used. Illustrative examples include chromosomal, non-chromosomal and synthetic DNA sequences, e.g., derivatives of SV40; plasmids (native or modified); phage DNA; baculovirus; yeast plasmids; vectors derived from combinations of plasmids and phage DNA, viral DNA such as vaccinia, adenovirus, fowl pox virus, pseudorabies, adenovirus, adeno-associated virus, retroviruses or the like.

When incorporated into an expression vector, the recombinant polynucleotides are operatively linked to an appropriate transcription control sequence (promoter) to direct mRNA synthesis. The promoters may be constitutive, leaky, or inducible, and native or non-native (e.g., exogenous or chimeric) to the methanotrophic strain employed. Examples of such transcription control sequences suited for use in the practice of the present disclosure include a pyruvate decarboxylase (PDC) promoter, a deoxyxylulose phosphate synthase promoter, a methanol dehydrogenase promoter (MDH) (such as, for example, the promoter in the upstream intergenic region of the mxaF gene from *Methylococcus capsulatus* Bath (Acc. No. MCA 0779) or the MDH promoter from *M. extorquens* (See Springer et al., *FEMS Microbiol. Lett.* 160:119 (1998)), a hexulose 6-phosphate synthase promoter (HPS), a ribosomal protein S16 promoter, a serine phosphoenolpyruvate carboxylase promoter, a T5 promoter, Trc promoter, a promoter for PHA synthesis (Foellner et al., *Appl. Microbiol. Biotechnol.* 40:2384(1993)), a pyruvate decarboxylase promoter (Tokuhiro et al., *Appl. Biochem. Biotechnol.* 131:795, (2006)), the lac operon Plac promoter (Toyama et al., *Microbiol.* 143:595, (1997)), a hybrid promoter such as Ptrc (Brosius et al., *Gene* 27:161 (1984)), promoters identified from native plasmid in methylotrophs, methanotrophs, and the like.

Additionally, suitable homologous or heterologous promoters for high expression of recombinant nucleic acid molecules may be utilized. For example, U.S. Pat. No. 7,098,005 describes the use of promoters for high expression in the presence of methane or methanol of a heterologous coding nucleic acid in $C_1$ metabolizing bacteria.

In certain embodiments, an inducible promoter system may be used in connection with the control of expression of the recombinant polynucleotides employed in the present disclosure. Inducible promoter systems employed in the practice of the present disclosure include the tetracycline inducible promoter system, the IPTG/lac operon inducible promoter system; a heat shock inducible promoter system; a metal-responsive promoter system; a nitrate inducible promoter system; a light inducible promoter system; an ecdysone inducible promoter system; the inducible/regulatable system described for use in methylotrophic and methanotrophic bacteria (see, e.g., U.S. Patent Appl. No. US 2010/0221813, which inducible/regulatable systems are incorporated herein in their entirety by reference), or the like.

The expression systems and expression vectors for use in the compositions and methods of the present disclosure optionally contain genetic elements, such as, for example, one or more ribosome binding sites for translation initiation and a transcription termination site (e.g., PinII), polyadenylation signals, restriction enzyme sites, multiple cloning sites, other coding segments, or the like. An expression vector also optionally includes appropriate sequences for amplifying expression, e.g., an enhancer.

Recombinant methods for expression of exogenous or heterologous nucleic acids in microbial organisms are well known in the art. Such methods can be found described in, for example, Sambrook et al., Molecular Cloning: A Laboratory Manual, Third Ed., Cold Spring Harbor Laboratory, New York (2001); and Ausubel et al., Current Protocols in Molecular Biology, John Wiley and Sons, Baltimore, Md. (1999), which methods are incorporated herein by reference in their entirety.

In certain embodiments, the strength and timing of expression of the recombinant polynucleotides may be modulated using methods known in the art to improve production of the desired protein. For example, varying promoter strength or nucleic acid copy number may be used to modulate expression levels. In another example, timing of expression may be modulated by using inducible promoter systems or polycistronic operons. For example, expression of a desired protein may occur during growth phase and stationary phase of culture or during stationary phase only. In another example, a desired protein may undergo ordered co-expression with other genes of interest.

Introduction of a recombinant nucleic acid into the host cell can be achieved in a variety of ways that are known in the art. For example, electroporation of C1 metabolizing bacteria has been previously described in, for example, Toyama et al., *FEMS Microbiol. Lett.* 166:1, 1998; Kim and Wood, *Appl. Microbiol. Biotechnol.* 48:105, 1997; Yoshida et al., *Biotechnol. Lett.* 23:787, 2001, and U.S. Pat. Appl. Pub. No. US 2008/0026005.

Bacterial conjugation, which refers to a particular type of transformation involving direct contact of donor and recipient cells, is more frequently used for the transfer of nucleic acids into $C_1$ metabolizing microorganisms. Bacterial conjugation involves mixing "donor" and "recipient" cells together in close contact with each other. Conjugation occurs by formation of cytoplasmic connections between donor and recipient bacteria, with unidirectional transfer of newly synthesized donor nucleic acid molecules into the recipient cells. A recipient in a conjugation reaction is any cell that can accept nucleic acids through horizontal transfer from a donor bacterium. A donor in a conjugation reaction is a bacterium that contains a conjugative plasmid, conjugative transposon, or mobilized plasmid. The physical transfer of the donor plasmid can occur through a self-transmissible plasmid or with the assistance of a "helper" plasmid. Conjugations involving $C_1$ metabolizing bacteria have been previously described in Stolyar et al., *Mikrobiologiya* 64:686, 1995; Motoyama et al., *Appl. Micro. Biotech.* 42:67, 1994; Lloyd et al., *Arch. Microbiol.* 171:364, 1999; PCT Publication No. WO 02/18617; and Ali et al., *Microbiol.* 152:2931, 2006.

Expression of heterologous nucleic acids in C1 metabolizing bacteria is known in the art (see, e.g., U.S. Pat. No. 6,818,424, U.S. Patent Appl. Pub. No. 2003/0003528). Mu transposon based transformation of methylotrophic bacteria has been described (Akhverdyan et al., *Appl. Microbiol. Biotechnol.* 91:857, 2011). A mini-Tn7 transposon system for single and multicopy expression of heterologous nucleic acids without insertional inactivation of host genes in *Methylobacterium* has been described (U.S. Patent Appl. Pub. No. US 2008/0026005).

Further genetic modifications to the $C_1$ metabolizing microorganism may be desired as described herein, which can be imparted using known methods. For example, various methods for inactivating, knocking-out, or deleting endogenous gene function in $C_1$ metabolizing bacteria may be used. Allelic exchange using suicide vectors to construct deletion/insertional mutants in slow growing $C_1$ metabolizing bacteria have also been described in, for example, Toyama and Lidstrom, *Microbiol.* 144:183, 1998; Stolyar et al., *Microbiol.* 145:1235, 1999; Ali et al., *Microbiol.* 152: 2931, 2006; Van Dien et al., *Microbiol.* 149:601, 2003.

The recombinant polynucleotide(s) may be optionally fused in frame to nucleic acids encoding secretion/localization sequences to target polypeptide expression to a desired cellular compartment, membrane, or organelle of a cell, or to direct polypeptide secretion to the periplasmic space or into the cell culture broth. Such sequences are known to those of skill in the art, and include secretion leader peptides, organelle targeting sequences (e.g., nuclear localization sequences, endoplasmic reticulum (ER) retention signals, mitochondrial transit sequences, perxisomal transit sequences, and chloroplast transit sequences), membrane localization/anchor sequences (e.g., stop transfer sequences, GPI anchor sequences), or the like.

Methods of Making and Using Methanotrophic Expression Systems

In other aspects, the present disclosure provides a method of making a proline auxotroph, the method comprising (a) introducing a chromosomal mutation into a parental methanotrophic microorganism to generate a population of mutagenized methanotrophic microorganisms; (b) culturing the population of mutagenized methanotrophic microorganisms in the presence of $C_1$ substrate (e.g., methane, methanol) under two independent culture conditions, wherein the first condition comprises culturing in a proline-containing culture medium and the second condition comprises culturing in a proline-free culture medium; and (c) selecting a mutagenized methanotrophic microorganism from the population of mutagenized methanotrophic microorganisms that is a proline auxotroph, the proline auxotroph exhibiting a growth phenotype of no growth in a proline-free culture medium. In some embodiments, the $C_1$ substrate is methane, natural gas or methanol.

In certain embodiments, the chromosomal mutation comprises an addition or a deletion mutation of an endogenous chromosomal proC gene (a deletion mutant is also referred to as ΔproC), wherein pyrroline-5-carboxylate reductase activity is eliminated or minimized. For example, a chromosomal mutation comprises a deletion of all or a portion of an endogenouse proC gene, wherein the deletion results in either no product being produced or a polypeptide lacking pyrroline-5-carboxylate reductase activity (e.g., a truncated pyrroline-5-carboxylate reductase). In still other embodiments, the chromosomal mutation comprises an inactivating substitution mutation (e.g., transition, transversion, nonsense, missense) in an endogenous chromosomal proC gene, wherein the encoded polypeptide lacks or has minimal pyrroline-5-carboxylate reductase activity.

In addition, the proline auxotrophy of a non-naturally occurring methanotrophic microorganism as described herein is useful for genetic manipulation experiments. Thus, in another aspect, the present disclosure provides a method for selecting transformed methanotrophic proline auxotrophs, the method comprising (a) culturing, in a proline-free culture medium and in the presence of a $C_1$ substrate, a population of methanotrophic proline auxotrophs transformed with a nucleic acid molecule construct having: (1) a first recombinant polynucleotide encoding a desired protein; and (2) a second recombinant polynucleotide encoding a pyrroline-5-carboxylate reductase, wherein the culturing is under conditions and for a time sufficient to allow expression of the first and second recombinant polynucleotides; and (b) selecting cells that grow in the proline-free culture medium, whereby cells that grow in the proline-free culture medium correspond to transformed cells.

In short, the transformation of a population of methanotrophic proline auxotrophs will result in a mixed population of untransformed (parental) and transformed (nucleic acid molecule construct containing) methanotrophic proline auxotrophs. Hence, culturing such a mixed population in the absence of proline will only allow the transformed cells to grow and such cells will only continue to grow if the plasmid is maintained—thus, such proline auxotrophs are plasmid-addicted methanotrophic cells of any of the embodiments described herein. In this method, proline complementation, which is provided by the nucleic acid construct having a recombinant polynucleotide encoding pyrroline-5-carboxylate reductase, provides the marker for transformant selection.

The proline auxotrophs of the present disclosure also provide useful hosts for the production of desired products from a methanotrophic expression system. Thus, another aspect of the present disclosure provides a method of producing a desired product from a proline-responsive methanotrophic expression system, in which the method comprises culturing a proline auxotroph of any of the embodiments described herein, wherein the auxotroph further comprises a recombinant polynucleotide, wherein the recombinant polynucleotide encodes a desired protein or the recombinant polynucleotide modifies expression of an endogenous protein, in the presence of a $C_1$ substrate and under culture conditions sufficient to promote expression of the recombinant polynucleotide, wherein culturing conditions comprise culturing the proline auxotroph in a proline-containing culture medium, and wherein the desired product is selected from a recombinant protein, an endogenous protein, a metabolite, or combinations thereof. In certain embodiments, the $C_1$ substrate is methane or methanol, and more typically, the $C_1$ substrate is methane. When a proline auxotroph is an obligate methanotroph, the $C_1$ substrate is methane. Suitable culturing conditions are described in more detail herein.

In certain embodiments, the recombinant polynucleotide encodes a metabolic pathway enzyme involved in the biosynthesis of a metabolite, and the desired product is a metabolite. Examples of pathway enzymes and metabolites are described herein.

In yet another aspect, the present disclosure provides a method of producing a desired product from a plasmid-addicted methanotrophic expression system, in which the method comprises culturing any of the embodiments of a plasmid-addicted methanotrophic expression system described herein in the presence of a $C_1$ substrate under culturing conditions and for a time sufficient to promote the expression of the first and second recombinant polynucleotides, wherein the product produced is a recombinant protein, an endogenous protein, a metabolite, or combinations thereof. In certain embodiments, the culture conditions comprise culturing in a proline-free culture medium. In certain embodiments, the desired product is a protein or a metabolite. In certain embodiments, for any of the methods for producing a desired product described herein, the culturing is in the presence of oxygen.

The above-described methods may comprise a further step of lysing the methanotrophic cells, concentrating the quantity of product in the culture medium, separating the product from the proline-sensitive methanotrophic production strain or culture medium, or any combination thereof. The desired protein may be an enzyme, a fluorescent protein (e.g., green fluorescent protein, and the like), a therapeutic protein (e.g., a mammalian ligand, a mammalian receptor, or variant thereof, and the like), a vaccine antigen, an antiparasitic protein, or the like. In some embodiments, the enzyme is an enzyme that participates in a metabolic pathway implicated in the biosynthesis of a metabolic product compound (i.e., "a metabolic pathway enzyme"), such as, for example, a vitamin, an alcohol, an amino acid, a sugar, an organic acid, an antioxidant, a nucleotide, a polyol, an antibiotic, or the like.

In certain embodiments, a recombinant polynucleotide encodes a metabolic pathway enzyme, and the desired product is a metabolic product compound. In some embodiments, the first and second or plurality of recombinant polynucleotides are under the control of a single promoter. In other embodiments, the first and second or plurality of recombinant polynucleotides are under the control of two or more separate promoters.

The proline-responsive and plasmid-addicted methanotrophic cells of the present disclosure may be cultured under a variety of culture conditions to promote the expression of the recombinant polynucleotide in the case of the proline-responsive system, and the first and second recombinant polynucleotides in the case of the plasmid-addicted systems, respectively. The culture medium employed in the methods may be a liquid or solid medium. When carrying out the selection methods of the present disclosure, the plasmid-addicted methanotrophic cells are typically cultured on a solid medium that contains proline. When used as a host expression system for the production of a desired product, the proline-responsive and plasmid-addicted methanotrophic cells are typically cultured in a liquid culture medium.

In further embodiment, the $C_1$ substrate or carbon feedstock is selected methane, methanol, syngas, natural gas or combinations thereof. More typically, a carbon feedstock is selected from methane or natural gas. Methods for growth and maintenance of methanotrophic microorganism cultures are well known in the art.

In certain embodiments, a desired product is produced during a specific phase of cell growth (e.g., lag phase, log phase, stationary phase, or death phase). In some embodiments, non-naturally occurring methotrophic proline auxotrophs as provided herein are cultured to a low to medium cell density ($OD_{600}$) and then production of a desired product is initiated. In some embodiments, a desired product is produced while the non-naturally occurring methotrophic proline auxotrophs are no longer dividing or dividing very slowly. In some embodiments, a desired product is produced only during stationary phase. In some embodiments, a desired product is produced during log phase and stationary phase.

The fermenter composition comprising lactate produced by non-naturally occurring $C_1$ metabolizing microorganism (e.g., methanotrophs, methylotrophs) provided herein may further comprise other organic compounds associated with biological fermentation processes. For example, biological by-products of fermentation may include one or more of alcohols, epoxides, aldehydes, ketones, esters, or a combination thereof. In certain embodiments, the fermenter composition may contain one or more of the following alcohols: methanol, ethanol, butanol, or propanol. Other compounds, such as $H_2O$, $CO$, $CO_2$, $N_2$, $H_2$, $O_2$, and unutilized carbon feedstocks, such as methane, ethane, propane, and butane, may also be present in the fermenter off-gas.

When culturing is done in a liquid culture medium, the gaseous $C_1$ substrates may be introduced and dispersed into a liquid culture medium using any of a number of various known gas-liquid phase systems as described in more detail herein below. When culturing is done on a solid culture medium, the gaseous C1 substrates are typically introduced over the surface of the solid culture medium.

Conditions sufficient to produce a desired product include culturing the non-naturally occurring methanotrophic proline auxotrophs at a temperature in the range of about 0° C. to about 55° C. In some embodiments, the culture temperature is in the range of about 25° C. to about 50° C. In some embodiments, the culture temperature is in the range of about 37° C. to about 50° C., and may be in the range of about 37° C. to about 45° C. Other conditions sufficient to produce a desired product (e.g., lactate) include culturing the non-naturally occurring $C_1$ metabolizing microorganism at a pH in the range of about 6 to about 9, or in the range of about 7 to about 8.

In certain embodiments, non-naturally occurring methanotrophic proline auxotrophs provided herein produce a desired product at about 0.001 g/L of culture to about 500 g/L of culture. In some embodiments, the amount of desired product produced is about 1 g/L of culture to about 100 g/L of culture. In some embodiments, the amount of desired product produced is about 0.001 g/L, 0.01 g/L, 0.025 g/L, 0.05 g/L, 0.1 g/L, 0.15 g/L, 0.2 g/L, 0.25 g/L, 0.3 g/L, 0.4 g/L, 0.5 g/L, 0.6 g/L, 0.7 g/L, 0.8 g/L, 0.9 g/L, 1 g/L, 2.5 g/L, 5 g/L, 7.5 g/L, 10 g/L, 12.5 g/L, 15 g/L, 20 g/L, 25 g/L, 30 g/L, 35 g/L, 40 g/L, 45 g/L, 50 g/L, 60 g/L, 70 g/L, 80 g/L, 90 g/L, 100 g/L, 125 g/L, 150 g/L, 175 g/L, 200 g/L, 225 g/L, 250 g/L, 275 g/L, 300 g/L, 325 g/L, 350 g/L, 375 g/L, 400 g/L, 425 g/L, 450 g/L, 475 g/L, or 500 g/L.

A variety of culture methodologies may be used for recombinant methanotrophic bacteria described herein. For example, methanotrophic bacteria may be grown by batch culture or continuous culture methodologies. In certain embodiments, the cultures are grown in a controlled culture unit, such as a fermenter, bioreactor, hollow fiber membrane bioreactor, or the like. Other suitable methods include classical batch or fed-batch culture or continuous or semi-continuous culture methodologies. In certain embodiments, the cultures are grown in a controlled culture unit, such as a fermenter, bioreactor, hollow fiber membrane bioreactor, and the like.

A classical batch culturing method is a closed system where the composition of the media is set at the beginning of the culture and not subject to external alterations during the culture process. Thus, at the beginning of the culturing process, the media is inoculated with the desired mutant methanotrophic microorganism and growth or metabolic activity is permitted to occur without adding anything further to the system. Typically, however, a "batch" culture is batch with respect to the addition of the methanotrophic substrate and attempts are often made at controlling factors such as pH and oxygen concentration. In batch systems, the metabolite and biomass compositions of the system change constantly up to the time the culture is terminated. Within batch cultures, cells moderate through a static lag phase to a high growth logarithmic phase and finally to a stationary phase where growth rate is diminished or halted. If untreated, cells in the stationary phase will eventually die. Cells in logarithmic growth phase are often responsible for the bulk production of end product or intermediate in some systems. Stationary or post-exponential phase production can be obtained in other systems.

The Fed-Batch system is a variation on the standard batch system. Fed-Batch culture processes comprise a typical batch system with the modification that the methanotrophic substrate is added in increments as the culture progresses. Fed-Batch systems are useful when catabolite repression is apt to inhibit the metabolism of the cells and where it is desirable to have limited amounts of the C1 substrate in the media. Measurement of the actual substrate concentration in Fed-Batch systems is difficult and is therefore estimated on the basis of the changes of measureable factors, such as pH, dissolved oxygen, and the partial pressure of waste gases such as $CO_2$. Batch and Fed-Batch culturing methods are common and known in the art (see, e.g., Thomas D. Brock, Biotechnology: A Textbook of Industrial Microbiology, $2^{nd}$ Ed. (1989) Sinauer Associates, Inc., Sunderland, Mass.; Deshpande, *Appl. Biochem. Biotechnol.* 36:227 (1992), which are both incorporated herein by reference.

Continuous cultures are "open" systems where a defined culture media is added continuously to a bioreactor and an equal amount of conditioned media is removed simultaneously for processing. Continuous cultures generally maintain the cells at a constant high liquid phase density where cells are primarily in logarithmic phase growth. Alternatively, continuous culture may be practiced with immobilized cells where the methanotrophic substrate and nutrients are continuously added and valuable products, by-products, and waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limited nutrient, such as the C1 substrate or nitrogen level, at a fixed rate and allow all other parameters to modulate. In other systems, a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes, as well as techniques for maximizing the rate of product formation, are well known in the art.

Liquid phase bioreactors (e.g., stirred tank, packed bed, one liquid phase, two liquid phase, hollow fiber membrane) are well known in the art and may be used for growth of non-naturally occurring microorganisms and biocatalysis.

By using gas phase bioreactors, substrates for bioproduction are absorbed from a gas by non-naturally occurring microorganisms, cell lysates or cell-free fractions thereof, rather than from a liquid. Use of gas phase bioreactors with microorganisms is known in the art (see, e.g., U.S. Pat. Nos. 2,793,096; 4,999,302; 5,585,266; 5,079,168; and 6,143,556; U.S. Statutory Invention Registration H1430; U.S. Pat. Appl. Pub. No. US 2003/0032170; Emerging Technologies in Hazardous Waste Management III, 1993, eds. Tedder and Pohland, pp. 411-428, all of which are incorporated herein by reference). Exemplary gas phase bioreactors include single pass system, closed loop pumping system, and fluidized bed reactor. By utilizing gas phase bioreactors, methane or other gaseous substrates is readily available for bioconversion by polypeptides with, for example, monooxygenase activity. In certain embodiments, methods for converting a gas into a desired product are performed in gas phase bioreactors. In further embodiments, methods for converting a gas into a desired product are performed in fluidized bed reactors. In a fluidized bed reactor, a fluid (i.e., gas or liquid) is passed upward through particle bed carriers, usually sand, granular-activated carbon, or diatomaceous earth, on which microorganisms can attach and grow. The fluid velocity is such that particle bed carriers and attached microorganisms are suspended (i.e., bed fluidization). The microorganisms attached to the particle bed carriers freely circulate in the fluid, allowing for effective mass transfer of substrates in the fluid to the microorganisms and increased microbial growth. Exemplary fluidized bed reactors include plug-flow reactors and completely mixed reactors. Uses of fluidized bed reactors with microbial biofilms are known in the art (e.g., Pfluger et al., *Bioresource Technol.* 102:9919, 2011; Fennell et al., *Biotechnol, Bioengin.* 40:1218, 1992; Ruggeri et al., *Water Sci. Technol.* 29:347, 1994; U.S. Pat. Nos. 4,032,407; 4,009,098; 4,009,105; and 3,846,289, all of which are incorporated herein by reference).

Methanotrophic microorganisms described in the present disclosure may be grown as an isolated pure culture, with a heterologous non-methanotrophic microorganism(s) that may aid with growth, or with one or more different strains or species of methanotrophic bacteria may be combined to generate a mixed culture.

In alternative embodiments, methods described herein use non-naturally occurring methanotrophic proline auxotrophs of the present disclosure or cell lysates thereof immobilized on, within, or behind a solid matrix. In further embodiments, the non-naturally occurring methanotrophic proline auxotrophs of the present disclosure, cell lysates or cell-free extracts thereof are in a substantially non-aqueous state (e.g., lyophilized). Recombinant microorganisms, cell lysates or cell-free fractions thereof are temporarily or permanently attached on, within, or behind a solid matrix within a bioreactor. Nutrients, substrates, and other required factors are supplied to the solid matrices so that the cells may catalyze the desired reactions. Recombinant microorganisms may grow on the surface of a solid matrix (e.g., as a biofilm). Recombinant microorganisms, cell lysates or cell-free fractions derived thereof may be attached on the surface or within a solid matrix without cellular growth or in a non-living state. Exemplary solid matrix supports for microorganisms include polypropylene rings, ceramic bio-rings, ceramic saddles, fibrous supports (e.g., membrane), porous glass beads, polymer beads, charcoal, activated carbon, dried silica gel, particulate alumina, Ottawa sand, clay, polyurethane cell support sheets, and fluidized bed particle carrier (e.g., sand, granular-activated carbon, diatomaceous earth, calcium alginate gel beads).

The foregoing and other aspects of the invention may be better understood in connection with the following non-limiting examples.

EXAMPLES

Example 1

Construction of *M. capsulatus* Proline Auxotroph

If not stated otherwise the following media and culture conditions were used in all examples and are referred to as "standard conditions."

*Escherichia coli* cultures were propagated at 37° C. in Lysogeny Broth (LB). Where necessary, LB medium was solidified with 1.5% (w/v) agar and/or supplemented with 30 µg/ml kanamycin. *M. capsulatus* Bath cultures were grown in 25 mL MM-W1 medium in 125 mL serum bottles containing a 1:1 (v/v) methane:air gas mixture. The composition of the medium MM-W1 was as follows: 0.8 mM $MgSO_4*7H_2O$, 10 mM $NaNO_3$, 0.14 mM $CaCl_2$, 1.2 mM $NaHCO_3$, 2.35 mM $KH_2PO_4$, 3.4 mM $K_2HPO_4$, 20.7 µM $Na_2MoO_4*2H_2O$, 1 µM $CuSO_4*5H_2O$, 10 µM $Fe^{III}$—Na-EDTA, and 1 mL per liter of trace metals solution (containing, per liter 500 mg $FeSO_4*7H_2O$, 400 mg $ZnSO_4*7H_2O$, 20 mg $MnCl_2*7H_2O$, 50 mg $CoCl_2*6H_2O$, 10 mg $NiCl_2*6H_2O$, 15 mg $H_3BO_3$, 250 mg EDTA). Phosphate, bicarbonate, and $Fe^{III}$—Na-EDTA were added after the media was autoclaved and cooled. Where necessary, liquid MM-W1 media was supplemented with 15 µg/ml kanamycin or 100 µg/ml L-proline (Sigma Aldrich). *M. capsulatus* Bath cultures were incubated with 250 rpm agitation at 42° C. When required, MM-W1 medium was solidified with 1.5% (w/v) agar and supplemented with 7.5 µg/ml kanamycin or 100 µg/ml L-proline. Agar plates were incubated at 42° C. in a gas-tight chamber containing a 1:1 (v/v) methane:air gas mixture.

Transformation of *M. capsulatus* Bath by Conjugation

*M. capsulatus* Bath wild type or mutant strains were grown under standard conditions for 24 h or until the culture reached an optical density at 600 nm ($OD_{600}$) of 1. 1.5 ml of this culture were pelleted, washed three times with MM-W1 medium and then re-suspended in 0.5 ml MM-W1. In parallel, an *Escherichia coli* S17-λ pir strain with the plasmid of choice to be transferred into *M. capsulatus* Bath was grown under standard conditions and in the presence of 30 µg/ml kanamycin for 16 h. The culture was diluted to an $OD_{600}$=0.05 and then grown further under standard conditions and in the presence of 30 µg/ml kanamycin until it reached an OD600 nm=0.5. 3 ml of the culture were pelleted, washed three times with MM-W1 medium and then combined with 0.5 ml of the *M. capsulatus* Bath suspension. The mixed suspension was pelleted, then re-suspended in 40 µl of MM-W1 medium and spotted onto dry MM-W1 agar plates containing 0.2% yeast extract. Plates were incubated for 48 h at 37° C. in the presence of a 1:1 mixture of methane and air. After 24 h, cells were re-suspended in 1 mL sterile MM-W1 medium and 100-4, aliquots (undiluted and 1:100 dilution) were spread onto MM-W1 agar plates containing 7.5 µg/mL kanamycin. The plates were incubated in gas-tight chambers containing a 1:1 mixture of methane and air and maintained at 42° C. The gas mixture was replenished every 2 days until colonies formed, typically after 5-7 days. Colonies were streaked onto MM-W1 agar plates containing 7.5 µg/mL kanamycin to confirm kanamycin resistance as well as to further isolate transformed *M. capsulatus* Bath cells from residual *E. coli* donor cells. The presence of the correct plasmid in *M. capsulatus* Bath was verified by PCR and sequencing.

Construction of a proC Deletion in *M. capsulatus* Bath

A proC (MCA1535) in-frame deletion was made by homologous recombination to yield *M. capsulatus* Bath strain 1911. The proC deletion construct was created by amplifying the two 750 bp regions flanking the proC gene using primer combinations:

(1) proC-50
(TATATTTTAGAGACGATGCCGCCGCCATTTTCATGC; SEQ ID NO.:
27) / proC-5I
(TGTTCAGTCGGGAGAAAAGGGGAAGCGATGGACCTGGGCTATCTCGTC)

(SEQ ID NO.: 28)
and (2) proC-30
(TATACCCCTGAGACGGGTACGGCAGAGAATCCGGGC)(SEQ ID NO.:
29) / proC-3I
(GACGAGATAGCCCAGGTCCATCGCCCCTTTTCTCCCGACTGAACAATTC

CG)(SEQ ID NO.: 30).

Subsequently, the two fragments were joined by using splicing overlap extension PCR. The deletion construct was then cloned into a suicide vector and transformed into the mobilizing strain *E. coli* S17-λ pir. The suicide vector contains a pUC-based origin of replication that is functional in *E. coli*, but non-functional in *M. capsulatus* Bath. Additional features of this suicide vector include an origin of transfer (oriT) required for conjugational transfer, a kanamycin resistance marker (KanR) for selection and a copy of the sacB gene for counter selection purposes. The suicide vector containing the deletion construct was then introduced into *M. capsulatus* Bath by conjugation. Single crossover events were selected for on MM-W1 agar containing 7.5 µg/ml of kanamycin and confirmed by colony PCR using two primer combinations: (1) primer proC-F (GGTCCGACCAT-TCCAGCCGG) (SEQ ID NO.:31) and primer proC-30 (SEQ ID NO.:29) and (2) primer proC-R (TCATCGGCGGCAACCCAGAG) (SEQ ID NO.:32) and primer proC-50 (SEQ ID NO.:27), where primer proC-F (SEQ ID NO.:31) and proC-R (SEQ ID NO.:32) will bind upstream and downstream of the proC flanking regions, respectively. Resolution of the integrated suicide vector by a second crossover event was performed with strains that had tested positive for a single crossover event. For this purpose, strains were grown in 2 ml MMW1 medium supplemented with 100 µg/ml L-proline for 48 h and were then plated onto MMW1 agar plates containing 5% (w/v) sucrose and 100 µg/ml L-proline. Deletion events were verified by colony PCR using primers proC-F (SEQ ID NO.:31) and proC-R (SEQ ID NO.:32) and sequencing.

Example 2

Construction of Addictive Plasmid and Transformation of ΔproC Mutant

Complementation of the ΔproC mutant was performed by expressing a copy of the native *M. capsulatus* Bath proC gene (MCA1535) in trans. For this purpose MCA1535 was cloned into three different expression plasmids (p169, p1610 and p1614). All three expression plasmids had the following genetic elements in common: a constitutive methanotroph-specific MDH promoter, a kanamycin selection marker (KanR), a pUC-based origin of replication (functional in *E. coli* but non-functional in *M. capsulatus* Bath), an oriV (origin of replication functional in *M. capsulatus* Bath), a trfA gene (required for replication initiation of oriV based plasmids) and an origin of transfer (oriT) which is required for conjugational transfer. The only feature that varied in the three expression plasmids was the identity of the ribosomal binding site (RBS) downstream of the MDH promoter leading to differential protein expression levels [low (p1610), medium (p1614) and high (p169)] of genes controlled by these promoter/RBS combinations. MCA1535 was introduced downstream of the RBS in p1610, p1614 and p169 using a TypIIS cloning strategy yielding plasmids p1613, p165 and p166, respectively. Subsequently, plasmids were transformed into *E. coli* S17-λpir, and then introduced into a *M. capsulatus* Bath ΔproC mutant by conjugation yielding strains 1911-13, 1911-5 and 1911-6, respectively. Plasmid containing proC mutant strains were selected on MM-W1 agar containing 7.5 µg/ml of kanamycin.

To test for complementation of the ΔproC mutant phenotype by providing a copy of native MCA1535 in trans, the following strains were grown in 25 ml MM-W1 cultures under standard conditions and assayed for growth at $OD_{600}$: (1) Strains 1911-13 (low), 1911-5 (medium) and 1911-6 (high)expressing a copy of proC at one of three different levels, (2) ΔproC mutant, and (3) wild type. In addition, wild type and ΔproC mutant strains were grown under standard conditions in 25 mL MM-W1 cultures supplemented with 100 µg/mL L-proline, and growth was measured at $OD_{600}$. All strains were inoculated at a starting $OD_{600}$ of 0.1 and were assayed for $OD_{600}$ up to 95 h post-inoculation.

Figure 3:
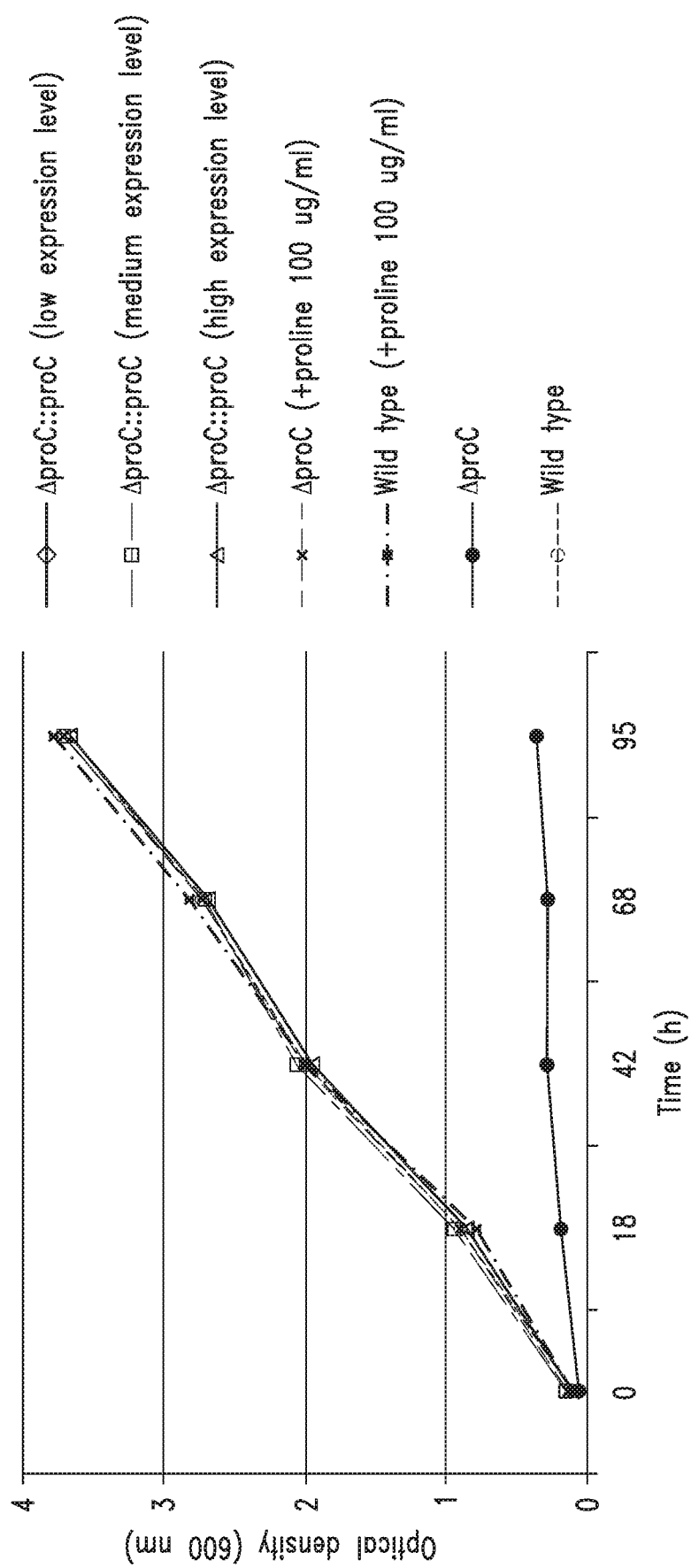
FIG. 3 depicts the impact of complementation of ΔproC *M. capsulatus* Bath mutants with: (1) the native *M. capsulatus* Bath proC gene (MCA1535) provided in trans (ΔproC:proC) in three different plasmids; and (2) 100 μg/mL proline, as compared to the following controls: (1) wildtype *M. capsulatus* Bath with no complementation; (2) wildtype *M. capsulatus* Bath complemented with 100 μg/mL proline; and (3) ΔproC *M. capsulatus* Bath mutant with no complementation, as described in Example 2.

FIG. 3 shows that expressing a copy of MCA1535 in a ΔproC mutant (blue diamond, red square and green triangle) successfully restored the ΔproC mutant growth phenotype when compared to wild type (blue bar) and a ΔproC mutant strain that was grown in the presence (purple cross) and absence (orange sphere) of 100 µg/mL L-proline. Furthermore, addition of up to 100 µg/mL L-proline to the growth medium of a wild type culture did not cause a growth phenotype (blue asterisks). In addition, an empty vector control was unable to restore a ΔproC mutant phenotype in the absence of proline (data not shown).

These results indicate that MCA1535 encodes a pyrroline-5-carboxylate reductase activity in *M. capsulatus* Bath and that the growth phenotype of a ΔproC mutant can be rescued either by externally supplying L-proline in the medium or by expressing a copy of native MCA1535 on a plasmid.

Example 3

Construction of Addictive Plasmid Containing Gene of Interest

Figure 4A:
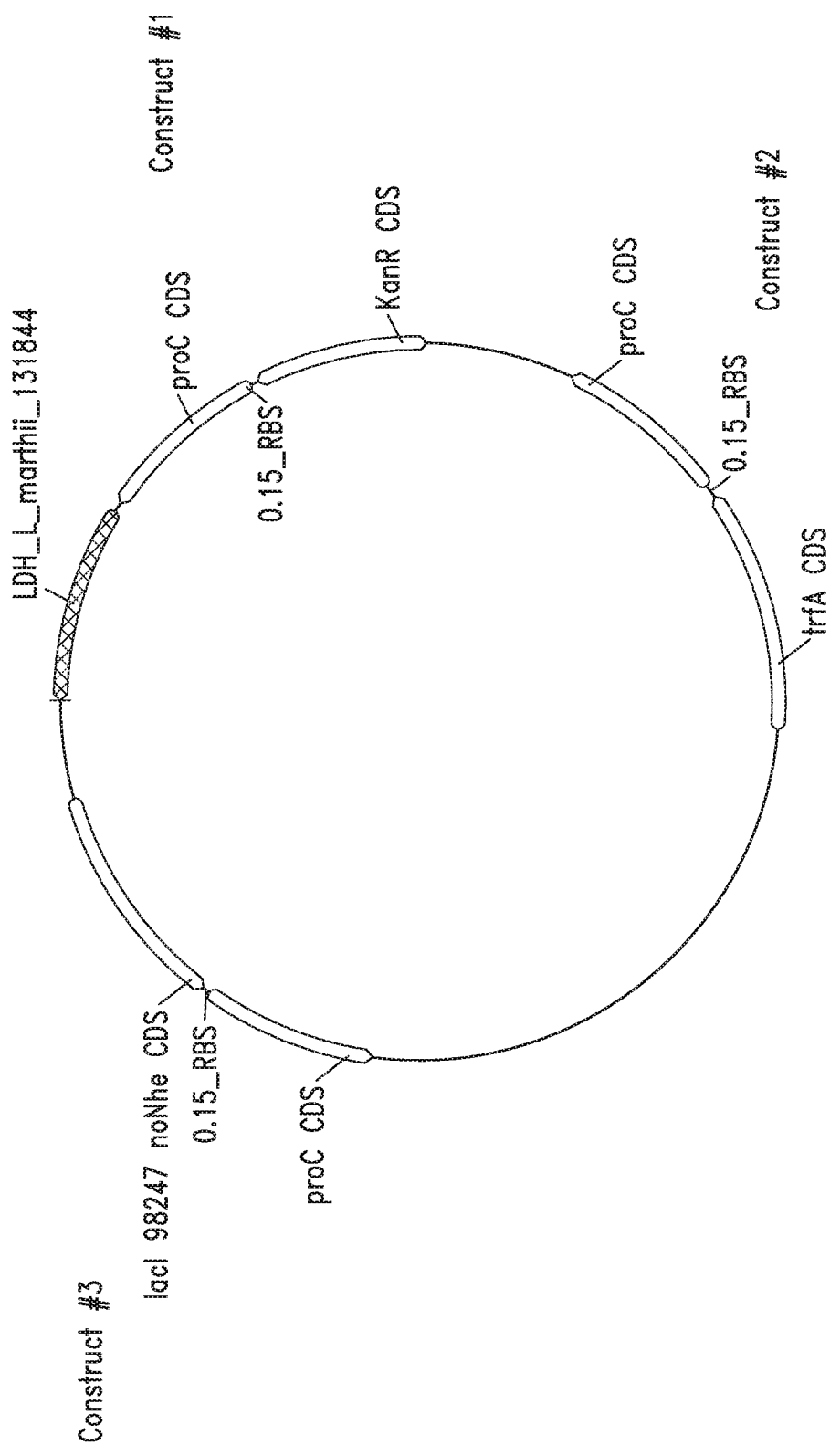
FIG. 4A depicts three constructs of a kanamycin-free addictive plasmid that were each constructed by assembly of the promoterless MCA1535 (proC) construct with an LDH expression plasmid, wherein the MCA1535 was inserted as follows: (Construct 1) downstream of the kanR gene yielding pLAP36 (pLA23 based) or pLAP42 (pLA30 based); (Construct 2) downstream of the trfA gene yielding pLAP38 (pLA23 based); and (Construct 3) downstream of the lacI gene yielding pLAP37 (pLA23 based).
Figure 4B:
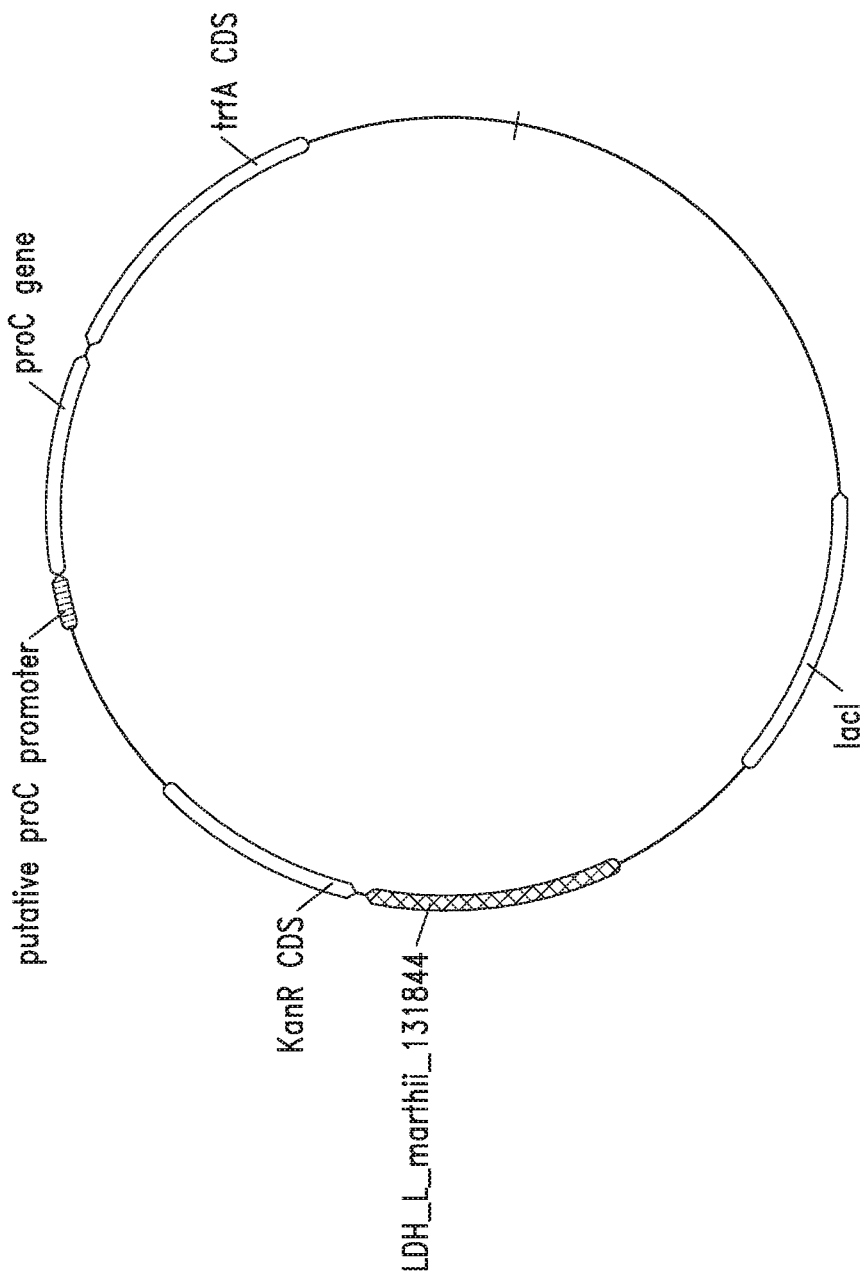
FIG. 4B depicts a fourth addictive plasmid (B) was constructed by cloning MCA1535 under the control of its native promoter using SacI/KpnI restriction sites on pLA29 to generate plasmid pLAP44.

Construction of addictive plasmids was performed by adding a copy of the native *M. capsulatus* Bath proC gene (MCA1535) into a lactate dehydrogenase (LDH) expressing plasmid (pLA23, pLA29 or pLA30). These expression vectors contained a LDH which was under control of the IPTG inducible methanotroph-specific MDH promoter. Additional genetic elements on this plasmid included a lacI gene under control of the methanotroph-specific MP10 promoter, a kanamycin selection marker (KanR), a pUC-based origin of replication (functional in *E. coli* but non-functional in *M. capsulatus* Bath), an oriV (origin of replication functional in *M. capsulatus* Bath), a trfA gene (required for replication initiation of oriV based plasmids) and an origin of transfer (oriT) which was required for conjugational transfer. Four versions of the addictive plasmid were constructed by either two-part Gibson assemblies of the promoterless MCA1535 and a LDH expression plasmid (Gibson et al., *Nature Methods* 6:343, 2009), or by standard restriction enzyme cloning. MCA1535 was inserted in an operon as follows: (1) downstream of the kanR gene yielding pLAP36 (pLA23 based) or pLAP42 (pLA30 based); (2) downstream of the trfA gene yielding pLAP38 (pLA23 based); and (3) downstream of the lacI gene yielding pLAP37 (pLA23 based), to ensure constitutive expression from the respective upstream promoters (see FIG. 4A). A fourth addictive plasmid was constructed by cloning MCA1535 under the control of its native promoter using SacI/KpnI restriction sites on pLA29 to generate plasmid pLAP44 (see FIG. 4B). Primers for amplification of the vector backbone were designed upstream (reverse primer) and downstream (forward primer) of the MCA1535 insertion site. 20-bp homology with the 5' and 3' ends of MCA1535 was added to each primer. Primers for amplification of promoterless MCA1535 were designed and 20-bp homology with the 5' and 3' ends of the vector backbone was added to each primer (primers used for the construction of pLAP36, pLAP37, pLAP38, and pLAP42 are provided in Table 2). Gibson assembly reactions were performed according to standard conditions and the assembled plasmids where then transformed into *E. coli* S17-λpir. MCA1535 and its native promoter was amplified from genomic DNA and cloned into the SacI/KpnI restriction site of pLA29 (primers used for construction of pLAP44 can be found in Table 2). Subsequently, plasmids were introduced into the *M. capsulatus* Bath ΔproC mutant by conjugation yielding strains 1911-36, 1911-37, 1911-38, 1911-42 and 1911-44, respectively. The presence of the correct plasmid in *M. capsulatus* Bath was verified by PCR and sequencing.

Functionality of the proline-based addiction system was assessed by testing strains for their ability to produce L-lactic acid in the absence of kanamycin selection pressure during growth. For this purpose strains 1911-36, 1911-37, and 1911-38 (ΔproC mutant strains expressing proC from constructs pLAP36, pLAP37, pLAP38, respectively) were used to inoculate 2.5 mL MM-W1 media/well of 24-well plates. In parallel, a wild type strain expressing pLA23 (strain 1911-23) was used to inoculate 2.5 ml MM-W1 media/well of a 24-well plate supplemented with 15 µg/ml kanamycin. The plate headspace was flushed with a 1:1 mixture of oxygen and methane as the carbon source for *M. capsulatus* Bath, the plates were sealed and then shaken continuously at a rate of 200-250 rpm during incubation at 42° C. for a 24 hour pre-culture. Then, new 24-well plates containing 2.5 ml fresh MM-W1, and where necessary 15 µg/ml kanamycin, were inoculated with 0.25 ml of the pre-culture and incubated at 42° C. for 72 hours. All strains were grown in two sets of triplicates, wherein one set was induced 24 h post-transfer with 5 mM IPTG and the other set was left un-induced. Post-induction (48 h) $OD_{600}$ readings of all cultures were taken, cells were then harvested by centrifugation, and supernatants were analyzed for L-lactic acid using the EnzyChrom™ lactate assay kit as per the manufacturer's instructions (BioAssay Systems).

In a parallel experiment, strains 1911-36, 1911-42 and 1911-44 (ΔproC mutant strains expressing proC from constructs pLAP36, pLAP42 or pLAP44, respectively) were used to inoculate 2.5 mL MM-W1 media/well of 24-well plates. The plates were sealed and incubated at 42° C. while continuously fed with a 1:1 mixture of oxygen and methane as the carbon source. The plates were shaken at a rate of 300 rpm for 24 hours (pre-culture). The total gas flow to the system was 100 ml/min corresponding to 25 ml/min to each tower. The plates were shaken continuously at 300 rpm on an 8 mm orbit for 24 h (pre-culture). Then, new 24-well plates containing 2.25 ml fresh MM-W1, were inoculated with 0.25 ml of the pre-culture and incubated at 42° C. for 72 h. All strains were grown in two sets of triplicates whereas one set was induced 24 h post-transfer with 5 mM IPTG whereas the other set was left un-induced. Post-induction (48 h) $OD_{600}$ readings of all cultures were taken, cells were then harvested by centrifugation, and supernatants were analyzed for L-lactic acid using the EnzyChrom™ lactate assay kit as per the manufacturer's instructions (BioAssay Systems).

Figure 5A:
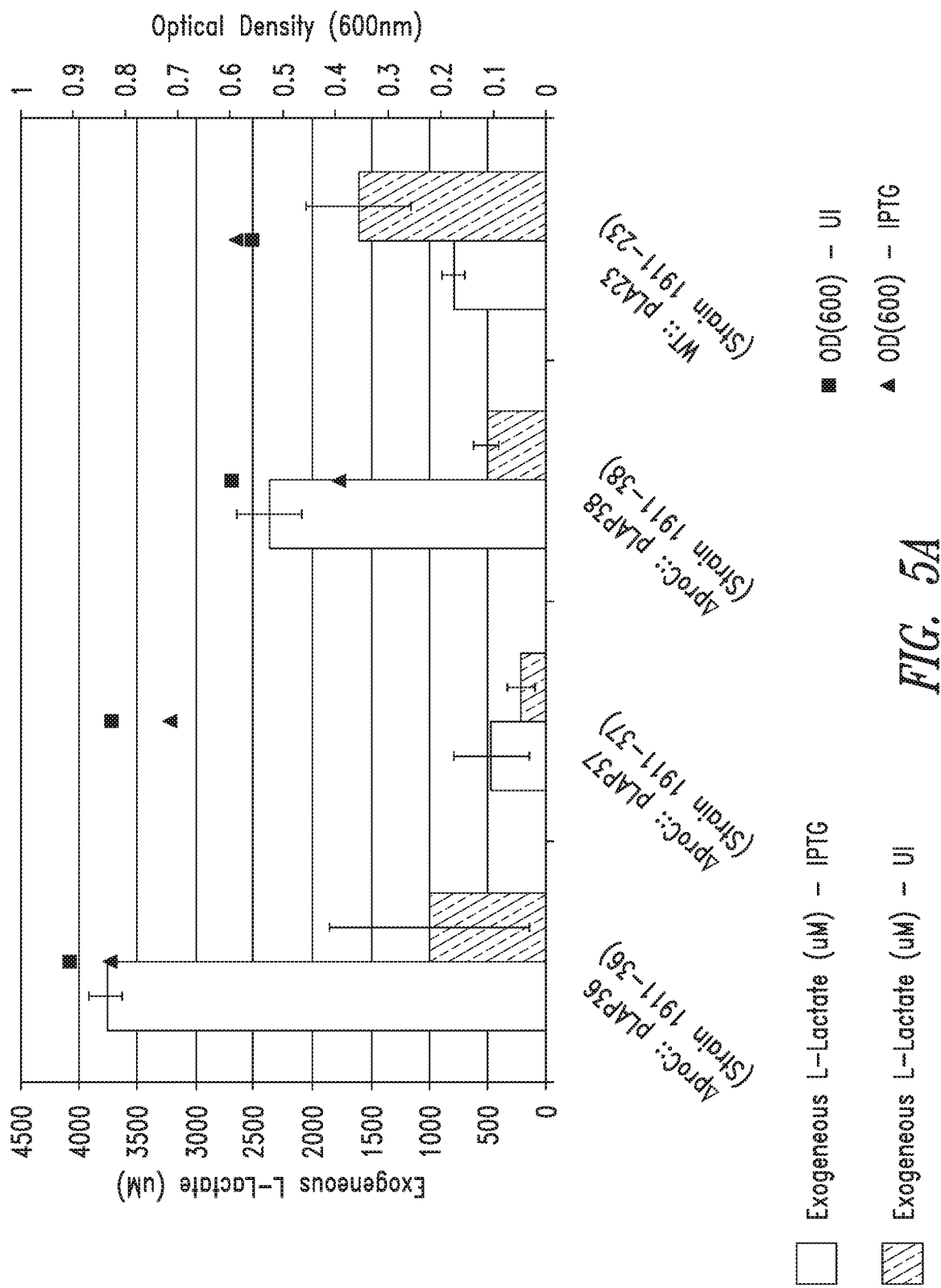
FIG. 5A depicts the production of a metabolite (L-lactate) and optical density of a mutant ΔproC *M. capsulatus* Bath transformed with a plasmid having the native *M. capsulatus* Bath proC gene and a gene of interest (lactate dehydrogenase (ldh)) under the control of the IPTG inducible methanotroph-specific MDH promoter, in which: (1) native *M. capsulatus* Bath proC gene (MCA1535) inserted downstream of the kanR gene (plasmid pLAP36); (2) MCA1535 inserted downstream of the trfA gene (plasmid pLAP38); or (3) MCA1535 inserted downstream of the lacI gene to facilitate constitutive expression from the respective upstream promoters (plasmid pLAP37), as described in Example 3. The strains were cultured in the absence of kanamycin selection pressure during growth. Also depicted is the control, wild type *M. capsulatus* Bath transformed with lactate dehydrogenase (LDH) expressing plasmid pLA23, cultured with 15 μg/mL kanamycin.

FIG. 5A shows exogenous production of L-lactic acid by strains 1911-36, 1911-37, 1911-38 and 1911-23 and corresponding $OD_{600}$ data at 72 h under both un-induced and induced conditions. Data represent an average of triplicate samples. Strains 1911-36, 1911-37, and 1911-38 were grown in the absence of kanamycin selection and plasmids in these strains were maintained by the proline-based addiction system. Strain 1911-23 was grown in the presence of 15 µg/ml kanamycin and served as the control. The data showed that strains whose plasmids where maintained by proline addiction generally reached higher L-lactic acid titers and $OD_{600}$ than the control strain. Specifically, under induced conditions strain 1911-36 produced about five times and strain 1911-38 produced about three times more L-lactic acid when compared to the control. Both strains also reached comparable or higher final ODs than the control strain. Strain 1911-37 produced similar concentrations of L-lactic and showed comparable $OD_{600}$ when compared to the control. Under un-induced conditions comparable amounts of L-lactic acid where detected in the culture supernatant of strain 1911-36 and the control, whereas strains 1911-37 and 1911-38 leaked approximately four to eight times less L-lactic acid into the culture medium.

In summary, these experiments show that the proline-based addiction system is functional in *M. capsulatus* Bath and that it performs similar or better when compared to kanamycin selection.

Figure 5B:
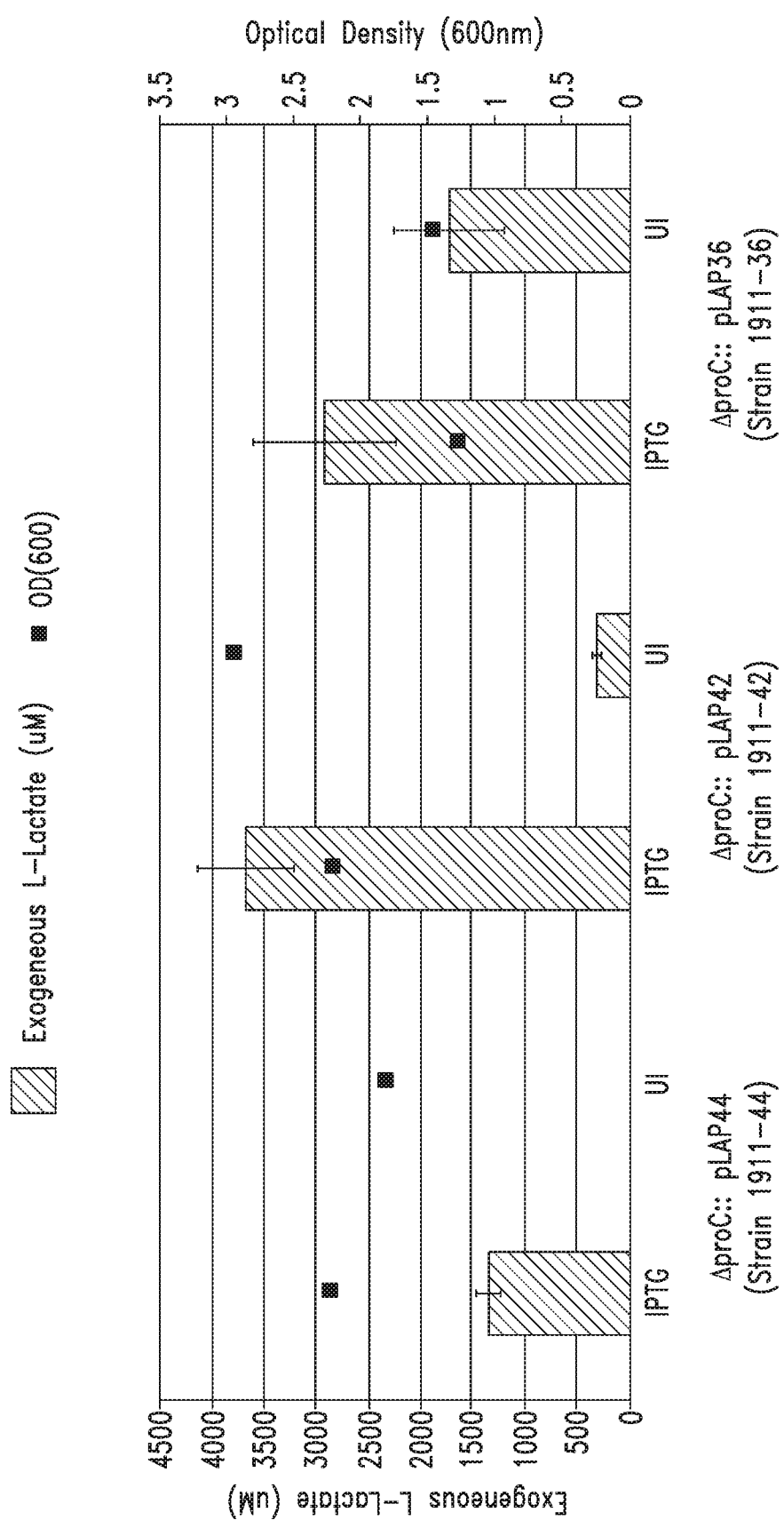
FIG. 5B depicts the production of L-lactic acid from strains 1911-36, 1911-42 and 1911-44 and corresponding $OD_{600}$ data at 72 h under both un-induced and induced conditions, as described in Example 3. UI means uninduced.

FIG. 5B shows L-lactic acid production of strains 1911-36, 1911-42 and 1911-44 and corresponding $OD_{600}$ data at 72 h under both un-induced and induced conditions. Data represent an average of triplicate samples. Under conditions of continuous methane and oxygen feed, strain 1911-36 produced around 3 mM of L-lactic acid under induced conditions and 1.7 mM L-lactic acid under un-induced conditions, which is comparable to L-lactic acid titers from the same strain shown in FIG. 5A grown under batch feeding conditions. Strain 1911-42, which is identical to strain 1911-36 except that the LDH is expressed at higher levels and controlled more tightly, produced 3.6 mM L-lactic acid under induced conditions and 0.3 mM L-lactic acid under un-induced conditions. Both strain 1911-36 and 1911-42 expressed the proC gene from the constitutive KanR promoter. Strain 1911-44, in contrast, expressed the proC gene from its native Bath promoter and showed that expression from this promoter supports maintenance of the addictive plasmid in the absence of Kanamycin as selection pressure. Strain 1911-44 produced 1.3 mM of L-lactic acid under induced conditions. L-lactic acid production under un-induced conditions was below the detection limit of the assay used.

TABLE 2

Primer Sequences Used for Plasmid Construction

| Plasmid Constructed | Primer (SEQ ID NO.) | Primer (5'-3') |
|---|---|---|
| pLAP36, pLAP42 | PuL3 (33) | TTTTTATTTTTTACATCCATGGGGCCCG GGTTAGAAAAA |
| | PuL5R (34) | CGCGGGAACTGGGGGCTTGATCGTCTT CGAATTCGGGGTT |
| | PuL5F (35) | AACCCCGAATTCGAAGACGATCAAGCC CCCAGTTCCCGCG |
| | PuL3R (36) | GTTTTTCTAACCCGGGCCCCATGGATGT AAAAAATAAAAA |
| pLAP37 | PdI3F (37) | TTTTTATTTTTTACATCCATGCTAGCTT ACTGACCGCTTT |
| | PdI5R (38) | CGCGGGAACTGGGGGCTTGAGAATTCG AAGACGAAAAACC |
| | PdI5F (39) | GGTTTTTCGTCTTCGAATTCTCAAGCCC CCAGTTCCCGCG |
| | PdI3R (40) | AAAGCGGTCAGTAAGCTAGCATGGATG TAAAAAATAAAAA |
| pLAP38 | PdT3F (41) | TTTTTATTTTTTACATCCATGGTACCAA GCTTGAATTCGG |
| | PdT5R (42) | CGCGGGAACTGGGGGCTTGAGGTACCC CATGGGCTAGCGA |
| | PdT5F (43) | TCGCTAGCCCATGGGGTACCTCAAGCC CCAGTTCCCGCG |
| | PdT3R (44) | CCGAATTCAAGCTTGGTACCATGGATG TAAAAAATAAAAA |
| pLAP44 | PpF-Sac (45) | TATATAGAGCTCGCTGGAAGGACTCGG GATGCC |
| | PpR-Kpn (46) | TATATAGGTACCTCAAGCCCCCAGTTC CCGC |

Quantification of Proline

Proline was quantitated in cell culture supernatants following a modified method described by Sue et al. (*Appl. Environ. Microbiol.* 77:7605, 2011) using methyl chloroformate derivatization and subsequent analysis by gas chromatography with mass spectrometric detection (GC-MS). This treatment produced methyl esters of carboxylic acids and carbamates of amino acids, and added 14 mass units to each carboxyl group and 58 mass units to each primary and secondary amine group present on the target molecule.

To prepare samples for analysis, 200 µL aliquots of cell-free supernatant were treated with a series of chemical reagents in a stepwise manner with mixing by vortex (1,200 RPM, 1 min) between each step. The reagent additions were as follows: 20 d4-alanine (250 µM in deionized water), 35

μL sodium hydroxide (3N in deionized water), 42 μL pyridine, 170 μL methanol, 25 μL methyl chloroformate, 25 μL methyl chloroformate (a second addition), 400 μL chloroform, 400 μL sodium bicarbonate (50 mM in deionized water). Following derivatization, each sample was centrifuged at 10,000×g for 2 min. The organic phase was removed, transferred into a 1.5-mL microcentrifuge tube, and evaporated to dryness in a speedvac. Sample residues were then reconstituted in 60 μL of chloroform, mixed by vortex at 1,400×rpm for 1 minute, and transferred to an autosampler vial for analysis by GC-MS.

Analysis was performed using an Agilent 6890/5972 GC-MS system. The GC was equipped with an HP-SMS capillary column of 0.25 mm×30 m×0.25 μm dimensionality and received helium carrier gas at a flow rate of 1 ml/min. Oven temperature program started at 55° C. for 3 minutes, ramped to 325° C. at a rate of 20° C./min and was held at 325° C. for 2 minutes. Samples (1 μL) were injected using a Hamilton 10 μL autosampler syringe. The sample inlet was held at 250° C. and had a split ratio of 15:1, which was lined with a Restek Sky precision low pressure drop inlet liner packed with glass wool.

The L-proline derivative eluted from the column at 8.96 minutes and was quantitated using the 128 m/z characteristic ion. Compound identification was verified by monitoring the qualifier ion at 82 m/z and 19% abundance relative to the target ion. Calibration standards were prepared from analytical grade L-proline in deionized water. The calibration curve for L-proline was fitted using a non-weighted linear regression.

While specific embodiments of the invention have been illustrated and described, it will be readily appreciated that the various embodiments described above can be combined to provide further embodiments, and that various changes can be made therein without departing from the spirit and scope of the invention.

All of the U.S. patents, U.S. patent application publications, U.S. patent applications, foreign patents, foreign patent applications and non-patent publications referred to in this specification, including but not limited to U.S. Application No. 61/836,609, filed Jun. 18, 2013, U.S. Application No. 61/928,390, filed Jan. 16, 2014, and U.S. Application No. 62/160,896, filed May 13, 2015, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

That which is claimed is:

1. A non-naturally occurring proline auxotroph comprising an altered endogenous proC gene, wherein the proline auxotroph is *Methylococcus capsulatus*, and wherein the proline auxotroph exhibits a no growth phenotype when cultured in a proline-free culture medium and in the presence of a $C_1$ substrate.

2. The non-naturally occurring proline auxotroph of claim 1, wherein the proline auxotroph exhibits a growth phenotype when cultured in a proline-containing medium comprising from about 10 μg/mL to about 500 μg/mL of proline.

3. The non-naturally occurring proline auxotroph of claim 1, wherein the altered endogenous proC gene comprises a ΔproC mutation.

4. The non-naturally occurring proline auxotroph of claim 1, wherein the proline auxotroph further comprises a heterologous polynucleotide that encodes a desired protein.

5. The non-naturally occurring proline auxotroph of claim 4, wherein the encoded desired protein is:
   (a) a lactate dehydrogenase;
   (b) a propylene synthesis pathway enzyme;
   (c) an isoprene synthesis pathway enzyme;
   (d) a fatty acid converting enzyme;
   (e) a fatty acid elongation pathway enzyme;
   (f) an amino acid biosynthesis pathway enzyme; or
   (g) a carbohydrate biosynthesis pathway enzyme.

6. The non-naturally occurring proline auxotroph of claim 5, wherein:
   (a) the encoded propylene synthesis pathway enzyme is a crotonase, a crotonyl CoA thioesterase, or a 4-oxalocrotonate decarboxylase;
   (b) the encoded fatty acid converting enzyme is a fatty acyl-CoA reductase, a fatty alcohol forming acyl-ACP reductase, or a carboxylic acid reductase;
   (c) the encoded fatty acid elongation pathway enzyme is a β-ketoacyl-CoA synthase, a β-ketoacy-CoA reductase, a β-hydroxy acyl-CoA dehydratase, or an enoyl-CoA reductase;
   (d) the encoded amino acid biosynthesis pathway enzyme is a lysine biosynthesis enzyme, wherein the lysine biosynthesis enzyme is a, lysine-sensitive aspartokinase III (lysC), an aspartate kinase, an aspartate-semialdehyde dehydrogenase (asd), a dihydrodipicolinate synthase (dapA), a dihydrodipicolinate reductase (dapB), a 2,3,4,5-tetrahydropyridine-2,6-carboxylate N-succinyltransferase (dapD), an acetylornithine/succinyldiaminopimelateaminotransferase (argD), a succinyldiaminopimelate desuccinylase (dapE), a succinyldiaminopimelate transaminase, a diaminopimelate epimerase (dapF), or a diaminopimelate dicarboxylase (lysA);
   (e) the encoded amino acid biosynthesis pathway enzyme is a tryptophan biosynthesis enzyme, wherein the tryptophan biosynthesis enzyme is a chorismate-pyruvate lyase (ubiC), an anthranilate synthase component I (trpE), an anthranilate synthase component II (trpG), an anthranilate phosphoribosyltransferase (trpD), a phosphoribosylanthranilate isomerase (trpC), a tryptophan biosynthesis protein (trpC), an N-(5'phosphoribosyl) anthranilate isomerase (trpF), an indole-3-glycerol phosphate synthase, a tryptophan synthase alpha chain (trpA), or a tryptophan synthase beta chain (trpB);

the encoded amino acid biosynthesis pathway enzyme is a methionine biosynthesis enzyme, wherein the methionine biosynthesis enzyme is a homoserine O-succinyltransferase (metA), a cystathionine gamma-synthase (metB), a protein MalY, a cystathionine beta-lyase (metC), a B12-dependent methionine synthase (metH), or a 5-methyltetrahydropteroyltriglutamate-homocysteine S-methyltransferase (metE);

(g) the encoded amino acid biosynthesis pathway enzyme is a cysteine biosynthesis enzyme, wherein the cysteine biosynthesis enzyme is a serine acetyltransferase (CysE), a cysteine synthase A, or a cysteine synthase B; or (h) the encoded carbohydrate biosynthesis pathway enzyme is a pyruvate carboxylase, a phosphoenolpyruvate carboxykinase, an enolase, a phosphoglycerate mutase, a phosphoglycerate kinase, a glyceraldehyde-3-phosphate dehydrogenase, a Type A aldolase, a fructose 1,6-bisphosphatase, a phosphofructokinase, a phosphoglucose isomerase, a hexokinase, a glucose-6-phosphate, glucose-1-phosphate adenyltransferase, a glycogen synthase, or a glucan synthase.

7. The non-naturally occurring proline auxotroph of claim 4, wherein the heterologous polynucleotide is incorporated into a self-replicating nucleic acid construct or is integrated into the chromosome of the *Methylococcus capsulatus*.

8. The non-naturally occurring proline auxotroph of claim 1, wherein the proline auxotroph does not further comprise a recombinant polynucleotide encoding a proline transporter.

9. The non-naturally occurring proline auxotroph of claim 1, wherein the *Methylococcus capsulatus* comprises *Methylococcus capsulatus* Bath.

* * * * *

UNITED STATES PATENT AND TRADEMARK OFFICE
CERTIFICATE OF CORRECTION

| | | |
|---|---|---|
| PATENT NO. | : 10,995,316 B2 | Page 1 of 1 |
| APPLICATION NO. | : 15/573685 | |
| DATED | : May 4, 2021 | |
| INVENTOR(S) | : Jana Stumpe | |

It is certified that error appears in the above-identified patent and that said Letters Patent is hereby corrected as shown below:

In the Claims

Column 71, Claim 6, Line 3:
"the encoded amino acid"
Should read:
-- (f) the encoded amino acid --.

Signed and Sealed this
Twenty-fifth Day of January, 2022

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 46

<210> SEQ ID NO 1
<211> LENGTH: 825
<212> TYPE: DNA
<213> ORGANISM: Methylococcus capsulatus

<400> SEQUENCE: 1
atgaagcata agaccttggg gttcatcggg gcaggcaaca tggcctcgag cctggtggga      60
gggctggtgg ccgacggtta tccggcccgg accatttggg tgtcggacgt ggatgaggcg     120
aagctggacg cgctttctct gaagttcgga gtcaacgtga gcggggacaa ccggcaggtg     180
gcgagactgg cggaaatcct gatcctggcc gtgaagccgc agattctgcg ggaagtggcg     240
gaggggctgg ccgacatcgt tgcggaaacc cggccgctgg tcctgtcggt cgcggccggt     300
gtcgcagagt cctccctcga ccgctggctc ggcgcgacc aggccctcgt ccgctgcatg     360
ccgaacaccc cggctctggt caagagttcc gccaccgcgc tgcatgcgaa cggcaagacg     420
acctcagccc aacgtagcga ggccgaaagc atcctgcgcg ccgtcggtgt gaccgtctgg     480
gtcgagcggg aggaagcgct ggacgccgtc acggcgattt ccggcagcgg accggcctac     540
tttttcctgc tgatggaagc gatggaaaac gccgccgcca gcctggggct cgatcccgag     600
accgcacgcc tcttggtgca gcagacgcg ctcggagccg cccgcatcgc catcgagtcc     660
gaagaaggtc cggcccagct gcggcagagg gtgacctctc ccaagggaac gaccgagcgg     720
gcgatcggcg tgttcgagga gcggggggctg catgagatcg tgagagatgc cgtggcggcg     780
gctcatgcca gagcggtcga attggcgcgg gaactggggg cttga                     825

<210> SEQ ID NO 2
<211> LENGTH: 274
<212> TYPE: PRT
<213> ORGANISM: Methylococcus capsulatus
```

<400> SEQUENCE: 2

```
Met Lys His Lys Thr Leu Gly Phe Ile Gly Ala Gly Asn Met Ala Ser
1               5                   10                  15

Ser Leu Val Gly Gly Leu Val Ala Asp Gly Tyr Pro Ala Arg Thr Ile
            20                  25                  30

Trp Val Ser Asp Val Asp Glu Ala Lys Leu Asp Ala Leu Ser Leu Lys
        35                  40                  45

Phe Gly Val Asn Val Ser Gly Asp Asn Arg Gln Val Ala Arg Leu Ala
    50                  55                  60

Glu Ile Leu Ile Leu Ala Val Lys Pro Gln Ile Leu Arg Glu Val Ala
65                  70                  75                  80

Glu Gly Leu Ala Asp Ile Val Ala Glu Thr Arg Pro Leu Val Leu Ser
                85                  90                  95

Val Ala Ala Gly Val Ala Glu Ser Ser Leu Asp Arg Trp Leu Gly Gly
            100                 105                 110

Asp Gln Ala Leu Val Arg Cys Met Pro Asn Thr Pro Ala Leu Val Lys
        115                 120                 125

Ser Ser Ala Thr Ala Leu His Ala Asn Gly Lys Thr Thr Ser Ala Gln
130                 135                 140

Arg Ser Glu Ala Glu Ser Ile Leu Arg Ala Val Gly Val Thr Val Trp
145                 150                 155                 160

Val Glu Arg Glu Glu Ala Leu Asp Ala Val Thr Ala Ile Ser Gly Ser
                165                 170                 175

Gly Pro Ala Tyr Phe Phe Leu Leu Met Glu Ala Met Glu Asn Ala Ala
            180                 185                 190

Ala Ser Leu Gly Leu Asp Pro Glu Thr Ala Arg Leu Leu Val Gln Gln
        195                 200                 205

Thr Ala Leu Gly Ala Ala Arg Ile Ala Ile Glu Ser Glu Glu Gly Pro
210                 215                 220

Ala Gln Leu Arg Gln Arg Val Thr Ser Pro Lys Gly Thr Thr Glu Arg
225                 230                 235                 240

Ala Ile Gly Val Phe Glu Glu Arg Gly Leu His Glu Ile Val Arg Asp
                245                 250                 255

Ala Val Ala Ala Ala His Ala Arg Ala Val Glu Leu Ala Arg Glu Leu
            260                 265                 270

Gly Ala
```

<210> SEQ ID NO 3
<211> LENGTH: 828
<212> TYPE: DNA
<213> ORGANISM: Methylomonas methanica

<400> SEQUENCE: 3

```
ttaatcggct cccagttgtt tggacatttc aatggaacgg tctctcgccg ccagcaaggc      60
cttggacacc agctcgctaa agccgttttg ctgaaaagtt tcgatggctt ttgagtggt     120 accgccgggc gacgtcaccc tttcccgtaa ttgggtaggc gactcggccg attccagcgc    180
aattttagca gcgcccaagg cggtttgttg gaccaacaag cgggcagtat gttcattcaa    240
acccatctca atcgccgttt tttccattgc ttccatcatc agaaaaaaat aggccggacc    300
gctgccggac accgcgtca ccgcatcgag ctcctgttcg tgctctaccc ataacgagat     360
accgacagca cgtaaaatat tttcggccag atcttttttgc tcctcgttga cattggcatt    420
ggcatgcagg gccgtagcac cggttaatac caaggccggg gtattgggca tgcatcgcac    480
```

```
gatagcggta tcgccccca gccacaaagc caaactggtt tgagaaatac cggcggctat    540
ggataccacc agactatctt tttgtttaac cagcggagca atctgcaagg ctacttcccg    600
caatatctgc ggtttgaccg ccagcactac cacatccact tcctgcacga ttttttaaatt   660 atcggtggat gcattgacat taagattatc acgatgggct gcagggtag ccggagccgc    720 atcggacacc caaatttgtt gcggagaatg tccgctggcg attaaaccgc tcatcaagct    780
ggtggccatg tttccgccac cgataaaacc gattgttctt gttttcat              828
```

<210> SEQ ID NO 4
<211> LENGTH: 275
<212> TYPE: PRT
<213> ORGANISM: Methylomonas methanica

<400> SEQUENCE: 4

```
Met Lys Thr Arg Thr Ile Gly Phe Ile Gly Gly Asn Met Ala Thr
  1               5                  10                  15

Ser Leu Met Ser Gly Leu Ile Ala Ser Gly His Ser Pro Gln Gln Ile
                 20                  25                  30

Trp Val Ser Asp Ala Ala Pro Ala Thr Leu Gln Ala His Arg Asp Asn
             35                  40                  45

Leu Asn Val Asn Ala Ser Thr Asp Asn Leu Lys Ile Val Gln Glu Val
         50                  55                  60

Asp Val Val Leu Ala Val Lys Pro Gln Ile Leu Arg Glu Val Ala
 65                  70                  75                  80

Leu Gln Ile Ala Pro Leu Val Lys Gln Lys Asp Ser Leu Val Val Ser
                 85                  90                  95

Ile Ala Ala Gly Ile Ser Gln Thr Ser Leu Ala Leu Trp Leu Gly Gly
                100                 105                 110

Asp Thr Ala Ile Val Arg Cys Met Pro Asn Thr Pro Ala Leu Val Leu
            115                 120                 125

Thr Gly Ala Thr Ala Leu His Ala Asn Ala Asn Val Asn Glu Glu Gln
        130                 135                 140

Lys Asp Leu Ala Glu Asn Ile Leu Arg Ala Val Gly Ile Ser Leu Trp
145                 150                 155                 160

Val Glu His Glu Gln Glu Leu Asp Ala Val Thr Ala Val Ser Gly Ser
                165                 170                 175

Gly Pro Ala Tyr Phe Phe Leu Met Met Glu Ala Met Glu Lys Thr Ala
            180                 185                 190

Ile Glu Met Gly Leu Asn Glu His Thr Ala Arg Leu Leu Val Gln Gln
        195                 200                 205

Thr Ala Leu Gly Ala Ala Lys Ile Ala Leu Glu Ser Ala Glu Ser Pro
    210                 215                 220

Thr Gln Leu Arg Glu Arg Val Thr Ser Pro Gly Gly Thr Thr Gln Lys
225                 230                 235                 240

Ala Ile Glu Thr Phe Gln Gln Asn Gly Phe Ser Glu Leu Val Ser Lys
                245                 250                 255

Ala Leu Leu Ala Ala Arg Asp Arg Ser Ile Glu Met Ser Lys Gln Leu
            260                 265                 270

Gly Ala Asp
        275
```

<210> SEQ ID NO 5
<211> LENGTH: 828
<212> TYPE: DNA

<213> ORGANISM: Methylomicrobium album

<400> SEQUENCE: 5

```
atgaaaacac aaaaaattgg atttatcggc ggcggcaata tggcgacgag cctgatcagc      60
ggcctgatcg ctgccggtca tgagccttcc agcatctggg tttccgacat caactccgag     120
cagctcaagt cgctggcgga gcgtctgaaa gtcaacgtga ccgcatcgaa cgaaacggca     180
gtcagcgagg ccgacgtcgt cgtgctggcg gtgaagccgc agatcatgcg cgatgtggcg     240
aaacagatcg cgccggcgat tcagcagcgt aaaccactgg tcgtctcgat tgccgccggc     300
atcggcgagc gcagcctcag cgcctggctg gggccggaca tcgcgatcgt ccgctgcatg     360
ccgaatacgc cggcgttggt gctgaccggc gccacggccc tgcatgcgaa cgacaaagtc     420
ggtgccgagc agcgcagcat ggccgaaaac attttgcgtg cggtcggtat tgcgctttgg     480
gtcaaggatg aaaagaact ggatgcggta acggccgtat cgggcagcgg accggcttat     540
tacttcctgc tgatggaatc gatggagaaa gcggcggcgg agctgggcct gaccgaggaa     600
acggcgcgcc tgctggtgct gcaaaccgcc ttgggcgcgg caaaaattgc gctggaatcg     660
agcgaaaccc ctgagttgtt gcgcaaacgc gtgacctcgc cgggcggcac gactcagcgg     720
gcgatcgaaa cctttcagca aggcggtttc gaggcactgg tttcgaaagc gctccatgcg     780
gcacgcgacc gttcggtcga aatgtccaac caaccggagt tcaattaa                   828
```

<210> SEQ ID NO 6
<211> LENGTH: 275
<212> TYPE: PRT
<213> ORGANISM: Methylomicrobium album

<400> SEQUENCE: 6

```
Met Lys Thr Gln Lys Ile Gly Phe Ile Gly Gly Gly Asn Met Ala Thr
1               5                   10                  15

Ser Leu Ile Ser Gly Leu Ile Ala Ala Gly His Glu Pro Ser Ser Ile
            20                  25                  30

Trp Val Ser Asp Ile Asn Ser Glu Gln Leu Lys Ser Leu Ala Glu Arg
        35                  40                  45

Leu Lys Val Asn Val Thr Ala Ser Asn Glu Thr Ala Val Ser Glu Ala
    50                  55                  60

Asp Val Val Leu Ala Val Lys Pro Gln Ile Met Arg Asp Val Ala
65                  70                  75                  80

Lys Gln Ile Ala Pro Ala Ile Gln Gln Arg Lys Pro Leu Val Val Ser
                85                  90                  95

Ile Ala Ala Gly Ile Gly Glu Arg Ser Leu Ser Ala Trp Leu Gly Pro
            100                 105                 110

Asp Ile Ala Ile Val Arg Cys Met Pro Asn Thr Pro Ala Leu Val Leu
        115                 120                 125

Thr Gly Ala Thr Ala Leu His Ala Asn Asp Lys Val Gly Ala Glu Gln
    130                 135                 140

Arg Ser Met Ala Glu Asn Ile Leu Arg Ala Val Gly Ile Ala Leu Trp
145                 150                 155                 160

Val Lys Asp Glu Lys Glu Leu Asp Ala Val Thr Ala Val Ser Gly Ser
                165                 170                 175

Gly Pro Ala Tyr Tyr Phe Leu Leu Met Glu Ser Met Glu Lys Ala Ala
            180                 185                 190

Ala Glu Leu Gly Leu Thr Glu Glu Thr Ala Arg Leu Leu Val Leu Gln
        195                 200                 205
```

```
Thr Ala Leu Gly Ala Ala Lys Ile Ala Leu Glu Ser Ser Glu Thr Pro
    210                 215                 220

Glu Leu Leu Arg Lys Arg Val Thr Ser Pro Gly Gly Thr Thr Gln Arg
225                 230                 235                 240

Ala Ile Glu Thr Phe Gln Gln Gly Gly Phe Glu Ala Leu Val Ser Lys
                245                 250                 255

Ala Leu His Ala Ala Arg Asp Arg Ser Val Glu Met Ser Asn Gln Pro
            260                 265                 270

Glu Phe Asn
        275

<210> SEQ ID NO 7
<211> LENGTH: 828
<212> TYPE: DNA
<213> ORGANISM: Methylomicrobium alcaliphilum

<400> SEQUENCE: 7
ttattgttct cccaattgtt tggacatctc gatcgagcgg tcatgcgcgg cttgaatggc      60
cttggcgacc aactctcgga atcctccttg ttcgaaagct tgattgctt gttcggtggt     120
gccgccggc gaagagaccc gtttgcgcaa ttgttcgggg gactcgttcg attcgagcgc     180
gattttagcg gcgccgagcg cggtttgttg aatcagcaag cgtgccgtat gttcctgcat     240
gcccattgac aatgcggctt gttccatcgc ttccatcagc aaaaagtaat aggccgggcc     300
gctgcccgat accgcagtaa ccgcatcgag ttccgattct ttatcgaccc ataacgcaac     360
gccgaccgag cgtagaatat tttcagccaa gtcgcgctgt tcgtcgtcga cattcgcatt     420
ggcatgtaaa ccggttgcgc cggtcaacac caaggacggg gtatttggca tgcagcgcac     480
gacagcgact tcggcgccca gccagcggct cagactctct tgagcgatgc cggcggcgat     540
cgaaacgacc aacgggcgct ttttccgtat gctggccgcg cagttttccg cgacttcacg     600
tagtacctgt ggcttgattg ccagcacgac gacgtcgact tcctcgatga cggcttcatt     660
ggcaacggaa atattaatat ttaaattgtt tgccagcgtt ttaaggacgt cttgattgat     720
atccgagacc catatttgag atggcgagtg accgctggca atcaaacccg tgatgagact     780
ggaggccata ttgccgcctc cgataaatcc gatttttttc gttttcat                 828

<210> SEQ ID NO 8
<211> LENGTH: 275
<212> TYPE: PRT
<213> ORGANISM: Methylomicrobium alcaliphilum

<400> SEQUENCE: 8

Met Lys Thr Lys Lys Ile Gly Phe Ile Gly Gly Gly Asn Met Ala Ser
1               5                   10                  15

Ser Leu Ile Thr Gly Leu Ile Ala Ser Gly His Ser Pro Ser Gln Ile
            20                  25                  30

Trp Val Ser Asp Ile Asn Gln Asp Val Leu Lys Thr Leu Ala Asn Asn
        35                  40                  45

Leu Asn Ile Asn Ile Ser Val Ala Asn Glu Ala Val Ile Glu Glu Val
    50                  55                  60

Asp Val Val Leu Ala Ile Lys Pro Gln Val Leu Arg Glu Val Ala
65                  70                  75                  80

Glu Asn Cys Ala Ala Ser Ile Arg Lys Lys Arg Pro Leu Val Val Ser
                85                  90                  95

Ile Ala Ala Gly Ile Ala Gln Glu Ser Leu Ser Arg Trp Leu Gly Ala
            100                 105                 110
```

Glu Val Ala Val Val Arg Cys Met Pro Asn Thr Pro Ser Leu Val Leu
            115                 120                 125

Thr Gly Ala Thr Gly Leu His Ala Asn Ala Asn Val Asp Asp Glu Gln
        130                 135                 140

Arg Asp Leu Ala Glu Asn Ile Leu Arg Ser Val Gly Val Ala Leu Trp
145                 150                 155                 160

Val Asp Lys Glu Ser Glu Leu Asp Ala Val Thr Ala Val Ser Gly Ser
                165                 170                 175

Gly Pro Ala Tyr Tyr Phe Leu Leu Met Glu Ala Met Glu Gln Ala Ala
            180                 185                 190

Leu Ser Met Gly Met Gln Glu His Thr Ala Arg Leu Leu Ile Gln Gln
        195                 200                 205

Thr Ala Leu Gly Ala Ala Lys Ile Ala Leu Glu Ser Asn Glu Ser Pro
    210                 215                 220

Glu Gln Leu Arg Lys Arg Val Ser Ser Pro Gly Gly Thr Thr Glu Gln
225                 230                 235                 240

Ala Ile Lys Ala Phe Glu Gln Gly Gly Phe Arg Glu Leu Val Ala Lys
                245                 250                 255

Ala Ile Gln Ala Ala His Asp Arg Ser Ile Glu Met Ser Lys Gln Leu
            260                 265                 270

Gly Glu Gln
        275

<210> SEQ ID NO 9
<211> LENGTH: 834
<212> TYPE: DNA
<213> ORGANISM: Methylobacterium extorquens

<400> SEQUENCE: 9
tcagccggac aattcgcccg cccgccgccg cgcctcctcg accgcctcgc gcatcaggtc      60
gggcagcgcg ccctcgcgca tcagcacggc gagggcggct gcggtggtgc cgccgggcga     120
ggtcacgtcg cggcgcaatt gcccggcctc gcgggcatca gcgtcgagca gagcaccggc     180
ccccgcgacg gtggcgcggg cgagctgcgc cgacaggtcc ggcgggaggc cggccgacac     240
gccggcttcc gcgagtgctt ccgccagcag gaagacgtag gcggggccgg agcccgagac     300
cgcggtcacc gcatcgatca acgcttcgtc gtcgagccac gccacgaggc cggagctggc     360
gagcaacgcc tccgcgccct cccgcgcctg cgatccgacc tccgggctgc cgacggcgcc     420
ggtcgcgccc cggccgatgc tggcgggcag gttgggcatg cgcgcaccac ggcgcgggc     480 ggtcggcagg cgacgcttga ggtcggcgat ggtttttccc gccaggatcg agacgacgag     540
ggtgtccggg ccgatccatc cggccagcgc cggtgccgcc cgtcgagaa cctgcggctt     600 gatgccgagc accagcgctc cggccgggac ggcggcttcg ggattgaggc gcaaggcccg     660
ctcggcacag agcgtcgcga tctccgcgga gggttgcgga tcgacgaccg tcaccgcggc     720
ggggtcgagg ccgcccgcga gccagccccg cagcagcgcc gccccatct tgccggcgcc     780 ggccagaacc aggggcgtgg gaaaggcggt cggatcatcg ggtgcgcgcg tcat           834

<210> SEQ ID NO 10
<211> LENGTH: 277
<212> TYPE: PRT
<213> ORGANISM: Methylobacterium extorquens

<400> SEQUENCE: 10

Met Thr Arg Ala Pro Asp Asp Pro Thr Ala Phe Pro Thr Pro Leu Val

```
              1               5              10              15
            Leu Ala Gly Ala Gly Lys Met Gly Ala Ala Leu Leu Arg Gly Trp Leu
                             20                  25                  30
            Ala Gly Gly Leu Asp Pro Ala Ala Val Thr Val Val Asp Pro Gln Pro
                             35                  40                  45
            Ser Ala Glu Ile Ala Thr Leu Cys Ala Glu Arg Ala Leu Arg Leu Asn
                             50                  55                  60
            Pro Glu Ala Ala Val Pro Ala Gly Ala Leu Val Leu Gly Ile Lys Pro
            65                  70                  75                  80
            Gln Val Leu Asp Ala Ala Pro Ala Leu Ala Gly Trp Ile Gly Pro
                             85                  90                  95
            Asp Thr Leu Val Val Ser Ile Leu Ala Gly Lys Thr Ile Ala Asp Leu
                            100                 105                 110
            Lys Arg Arg Leu Pro Thr Ala Arg Ala Val Val Arg Ala Met Pro Asn
                            115                 120                 125
            Leu Pro Ala Ser Ile Gly Arg Gly Ala Thr Gly Ala Val Gly Ser Pro
                            130                 135                 140
            Glu Val Gly Ser Gln Ala Arg Glu Gly Ala Glu Ala Leu Leu Ala Ser
            145                 150                 155                 160
            Ser Gly Leu Val Ala Trp Leu Asp Asp Glu Ala Leu Ile Asp Ala Val
                            165                 170                 175
            Thr Ala Val Ser Gly Ser Gly Pro Ala Tyr Val Phe Leu Leu Ala Glu
                            180                 185                 190
            Ala Leu Ala Glu Ala Gly Val Ser Ala Gly Leu Pro Pro Asp Leu Ser
                            195                 200                 205
            Ala Gln Leu Ala Arg Ala Thr Val Ala Gly Ala Leu Leu Asp
                            210                 215                 220
            Ala Asp Ala Arg Glu Ala Gly Gln Leu Arg Arg Asp Val Thr Ser Pro
            225                 230                 235                 240
            Gly Gly Thr Thr Ala Ala Leu Ala Val Leu Met Arg Glu Gly Ala
                            245                 250                 255
            Leu Pro Asp Leu Met Arg Glu Ala Val Glu Glu Ala Arg Arg Arg Ala
                            260                 265                 270
            Gly Glu Leu Ser Gly
                            275

<210> SEQ ID NO 11
<211> LENGTH: 834
<212> TYPE: DNA
<213> ORGANISM: Methylobacterium extorquens

<400> SEQUENCE: 11
tcagccggac aattcgcccg cccgccgccg cgccgcctcg accgcctcgc gcatcaggtc      60
gggcagcgcg ccctcgcgca tcagcacggc gagggcggct gcggtggtgc cgccgggcga     120
ggtcacgtcg cggcgcaatt gcccggcctg cgggcatcg cgtcgagca gggcaccggc       180 ccccgcgacg gtggcgcggg cgagctgcgc cgacaggtcg ggcggcaggc cgccgccac     240 gccggcctcc gcgagtgctt ccgccagcag gaagacgtag gccgggccgg agcccgagac     300
cgcggtcact gcatcgatca acgcttcgtc gtcgagccac gccacgaggc cggagctggc     360
gagcaacgcc tccgcgcccg cccgcgcctg cggtccgacc tcgggctgc cgacggcgcc     420 ggtcgcgccc cggccgatgc tgcgggcag gttgggcatg gcgcgcacca cggcgcgggc     480
ggtcggcagg cggcgcttga ggtcggcgat ggtcttgccg ccaggatcg agacgacgag     540
```

```
ggtgtccggg ccgatccatc cggccagcgc cggtgccgcc gcgtcgagaa cctgcggctt    600
gatgccgagc accagcgctc cggccgggac ggcggcttcg ggattgaggc gcaaggcccg    660
ctcggcacag agtgtcgcga tctccgcgga gggctgcgga tcgacgacgg tcacggcggc    720
ggggtcgagg ccgcccgcga gccagccccg cagcagcgcc gctcccatct tgccggcgcc    780
ggccagaacc aggggcgtgg gaaaggcggt cggatcatcg ggcgcgcgcg tcat          834
```

<210> SEQ ID NO 12
<211> LENGTH: 277
<212> TYPE: PRT
<213> ORGANISM: Methylobacterium extorquens

<400> SEQUENCE: 12

```
Met Thr Arg Ala Pro Asp Asp Pro Thr Ala Phe Pro Thr Pro Leu Val
1               5                   10                  15

Leu Ala Gly Ala Gly Lys Met Gly Ala Ala Leu Leu Arg Gly Trp Leu
            20                  25                  30

Ala Gly Gly Leu Asp Pro Ala Ala Val Thr Val Val Asp Pro Gln Pro
        35                  40                  45

Ser Ala Glu Ile Ala Thr Leu Cys Ala Glu Arg Ala Leu Arg Leu Asn
    50                  55                  60

Pro Glu Ala Ala Val Pro Ala Gly Ala Leu Val Leu Gly Ile Lys Pro
65                  70                  75                  80

Gln Val Leu Asp Ala Ala Pro Ala Leu Ala Gly Trp Ile Gly Pro
                85                  90                  95

Asp Thr Leu Val Val Ser Ile Leu Ala Gly Lys Thr Ile Ala Asp Leu
            100                 105                 110

Lys Arg Arg Leu Pro Thr Ala Arg Ala Val Val Arg Ala Met Pro Asn
        115                 120                 125

Leu Pro Ala Ser Ile Gly Arg Gly Thr Gly Ala Val Gly Ser Pro
    130                 135                 140

Glu Val Gly Pro Gln Ala Arg Ala Gly Ala Glu Ala Leu Leu Ala Ser
145                 150                 155                 160

Ser Gly Leu Val Ala Trp Leu Asp Asp Glu Ala Leu Ile Asp Ala Val
                165                 170                 175

Thr Ala Val Ser Gly Ser Gly Pro Ala Tyr Val Phe Leu Leu Ala Glu
            180                 185                 190

Ala Leu Ala Glu Ala Gly Val Ala Ala Gly Leu Pro Pro Asp Leu Ser
        195                 200                 205

Ala Gln Leu Ala Arg Ala Thr Val Ala Gly Ala Gly Ala Leu Leu Asp
    210                 215                 220

Ala Asp Ala Arg Gln Ala Gly Gln Leu Arg Arg Asp Val Thr Ser Pro
225                 230                 235                 240

Gly Gly Thr Thr Ala Ala Ala Leu Ala Val Leu Met Arg Glu Gly Ala
                245                 250                 255

Leu Pro Asp Leu Met Arg Glu Ala Val Glu Ala Ala Arg Arg Arg Ala
            260                 265                 270

Gly Glu Leu Ser Gly
        275
```

<210> SEQ ID NO 13
<211> LENGTH: 834
<212> TYPE: DNA
<213> ORGANISM: Methylobacterium sp.

<400> SEQUENCE: 13

```
atggaccggt tccccatgaa cgcctccgat ctccccgcct ccctgatcct cgtcggcgcc    60
ggcaagatgg gcggggcgat gctggagggc tggctcgcgg gcgggctcga cgggtcgcgc   120
atcgcggtcg tggatcccgg cgcctccgcc gacctcgcgg atctctgcgc ccggcgcggc   180
atcgccctca acccgcaggg gttgacgccc cccgaggcgc tcgtgctcgc catcaagccg   240
caggggctgg aggcggccgc ccccgcggtc gcgcccctgg ccggtcccga cacgctcgtg   300
ctctcggtgc tggcgggcaa gacggtggcg aacctcaagg cccgcctgcc cgcggcgcgg   360
gccgtggtgc gggcgatgcc caacctgccg gcgagcatcg gcaaggggc caccggcgcg   420
gcggcgagcc ccgagaccag cgcccggcag cgccgcatgg ccgacgcgct cctctccggg   480
atcggcctcg tcgagtggct cgccgacgag agcctgatcg acgccgtcac ggcggtctcg   540
ggctccggcc cggcctacgt cttcctgctc gccgaggcgc tggccgaggc cggggcggcc   600
gcgggcctgc cgccggaggt cgccgcccgc ctcgcccgcc agaccgtcgc ggggcgggc   660
gcgctcctcg ccgagagccc cctcgatccc ggcaccctgc ccggaacgt gacctcgccg   720
ggcggcacca cggcggcggc gctcgccgtg ctgatggggg cgggcgggct gccggaccgc   780
ctgcgcgagg cggtggcggc ggccaggacc cgctcggcgg acctgtcggg ctga          834
```

<210> SEQ ID NO 14
<211> LENGTH: 277
<212> TYPE: PRT
<213> ORGANISM: Methylobacterium sp.

<400> SEQUENCE: 14

```
Met Asp Arg Phe Pro Met Asn Ala Ser Asp Leu Pro Ala Ser Leu Ile
1               5                   10                  15

Leu Val Gly Ala Gly Lys Met Gly Gly Ala Met Leu Glu Gly Trp Leu
            20                  25                  30

Ala Gly Gly Leu Asp Gly Ser Arg Ile Ala Val Val Asp Pro Gly Ala
        35                  40                  45

Ser Ala Asp Leu Ala Asp Leu Cys Ala Arg Arg Gly Ile Ala Leu Asn
    50                  55                  60

Pro Gln Gly Leu Thr Pro Pro Glu Ala Leu Val Leu Ala Ile Lys Pro
65                  70                  75                  80

Gln Gly Leu Glu Ala Ala Pro Ala Val Ala Pro Leu Ala Gly Pro
            85                  90                  95

Asp Thr Leu Val Leu Ser Val Leu Ala Gly Lys Thr Val Ala Asn Leu
            100                 105                 110

Lys Ala Arg Leu Pro Ala Ala Arg Ala Val Val Arg Ala Met Pro Asn
        115                 120                 125

Leu Pro Ala Ser Ile Gly Lys Gly Ala Thr Gly Ala Ala Ala Ser Pro
    130                 135                 140

Glu Thr Ser Ala Arg Gln Arg Arg Met Ala Asp Ala Leu Leu Ser Gly
145                 150                 155                 160

Ile Gly Leu Val Glu Trp Leu Ala Asp Glu Ser Leu Ile Asp Ala Val
                165                 170                 175

Thr Ala Val Ser Gly Ser Gly Pro Ala Tyr Val Phe Leu Leu Ala Glu
            180                 185                 190

Ala Leu Ala Glu Ala Gly Ala Ala Gly Leu Pro Pro Glu Val Ala
        195                 200                 205

Ala Arg Leu Ala Arg Gln Thr Val Ala Gly Ala Gly Ala Leu Leu Ala
    210                 215                 220
```

Glu Ser Pro Leu Asp Pro Gly Thr Leu Arg Arg Asn Val Thr Ser Pro
225                 230                 235                 240

Gly Gly Thr Thr Ala Ala Ala Leu Ala Val Leu Met Gly Ala Gly Gly
            245                 250                 255

Leu Pro Asp Arg Leu Arg Glu Ala Val Ala Ala Arg Thr Arg Ser
        260                 265                 270

Ala Asp Leu Ser Gly
        275

<210> SEQ ID NO 15
<211> LENGTH: 831
<212> TYPE: DNA
<213> ORGANISM: Methylobacterium populi

<400> SEQUENCE: 15
tcagccggac aattcgcccg cccggcgctt ggccgcagcg accgcctccc gcatcaggtc      60
gggcacggcc ccctcgcgca tcagcacggc gagcgccgcc gcggtggtgc cgccgggcga     120
ggtgacgtcc cggcgcagct gcccggcctc gcgggtatcg gcatcgagca gcgccccggc     180
gccggcgatg gtggcgcggg cgagctgggc cgacaggtcc ggcggaaggc ccgccgccac     240
gccggcttcc gcgagcgcct cggccagcag gaagacgtag gccgggccgg atcccgagac     300
cgcggtcacc gcgtcgatca gcgcctcgtc gtcgagccac gcgacgaggc cggagctggc     360
gagcagccgc tccgccccg cccgcgcctg cggcccgacc tcggggctgc cgacggcgcc     420
ggtcgcgccc cggccgatgc tggcgggcag gttgggcatg gcccgcacca ccgcgcgggc     480
ggccggcagg cggcgcttca ggtcggcgat ggtcttgccc gccaggatcg agacgacgag     540
ggtgtccggg ccgatccagg gcgagagcgc gggcgccgcc gcgtcgagaa cctgcggctt     600
gatcccgagc accagcgccc cggccggacc gtcggcgtgc gggttgaggc gcaaggcccg     660
ctcggcgcag agcccggcga tctcggggggc gggctgcgga tcgacgaccg tcaccgcggc     720
gggatcgaga ccgcccgcga gccagccgcg gagcagggcc gctcccatct gccggcacc      780 ggccagaacc agggggggtgg gaaaggcggt cggatcggtc gcgcgcgtca t              831

<210> SEQ ID NO 16
<211> LENGTH: 276
<212> TYPE: PRT
<213> ORGANISM: Methylobacterium populi

<400> SEQUENCE: 16

Met Thr Arg Ala Thr Asp Pro Thr Ala Phe Pro Thr Pro Leu Val Leu
1               5                   10                  15

Ala Gly Ala Gly Lys Met Gly Ala Ala Leu Leu Arg Gly Trp Leu Ala
            20                  25                  30

Gly Gly Leu Asp Pro Ala Ala Val Thr Val Val Asp Pro Gln Pro Ala
        35                  40                  45

Pro Glu Ile Ala Gly Leu Cys Ala Glu Arg Ala Leu Arg Leu Asn Pro
    50                  55                  60

His Ala Asp Gly Pro Ala Gly Ala Leu Val Leu Gly Ile Lys Pro Gln
65                  70                  75                  80

Val Leu Asp Ala Ala Ala Pro Ala Leu Ser Pro Trp Ile Gly Pro Asp
                85                  90                  95

Thr Leu Val Val Ser Ile Leu Ala Gly Lys Thr Ile Ala Asp Leu Lys
            100                 105                 110

Arg Arg Leu Pro Ala Ala Arg Ala Val Val Arg Ala Met Pro Asn Leu
        115                 120                 125

```
Pro Ala Ser Ile Gly Arg Gly Ala Thr Gly Ala Val Gly Ser Pro Glu
    130                 135                 140
Val Gly Pro Gln Ala Arg Ala Gly Ala Glu Arg Leu Leu Ala Ser Ser
145                 150                 155                 160
Gly Leu Val Ala Trp Leu Asp Asp Glu Ala Leu Ile Asp Ala Val Thr
                165                 170                 175
Ala Val Ser Gly Ser Gly Pro Ala Tyr Val Phe Leu Leu Ala Glu Ala
            180                 185                 190
Leu Ala Glu Ala Gly Val Ala Ala Gly Leu Pro Pro Asp Leu Ser Ala
        195                 200                 205
Gln Leu Ala Arg Ala Thr Ile Ala Gly Ala Gly Ala Leu Leu Asp Ala
    210                 215                 220
Asp Thr Arg Glu Ala Gly Gln Leu Arg Arg Asp Val Thr Ser Pro Gly
225                 230                 235                 240
Gly Thr Thr Ala Ala Ala Leu Ala Val Leu Met Arg Glu Gly Ala Val
                245                 250                 255
Pro Asp Leu Met Arg Glu Ala Val Ala Ala Lys Arg Arg Ala Gly
            260                 265                 270
Glu Leu Ser Gly
        275

<210> SEQ ID NO 17
<211> LENGTH: 834
<212> TYPE: DNA
<213> ORGANISM: Methylobacterium radiotolerans

<400> SEQUENCE: 17
tcagccggac agttccccccg cccgccgacg ggccgcggcc acggcctccc gcatcagcgc      60
gccgaggccg tccggccgca tcagcacctc gagggccgcc gcggtcgtgc cgccgggcga     120
cgtgacgttg cggcgcaact ccgccgcctc ggccgggctg catcgagga gcgcgccggc      180
ccccgccacg gtcgcccggg cgaggctgcg gcgacctca ggttccaggc cggccgcgat     240
gccggcctcc gccagggtct cggccagcag gaagacgtag gccggtccgg agcccgagac     300
cgccgtcacc gcgtcgatct cgcctcgtc ggtgagccac gccaccgcgc cgttcgcggc     360
gagcagcgcc tcggcggccg cccgctgcgc cggggtgacc tcggggctcg cgcaggcgcc     420
ggtggcgccc cggccgatgc tcgccgggag gttgggcatc gcccgacga tcgcgcgcgc     480
ccgcggcagc cggccgcgga tccgcgac ggtcttgccg gccaggatcg agacgaggag     540
cgtgtcgcgg ccgatgagcc ggtcgagccc ggggccgcc gtgtccaggc cctgcggctt     600
gatccccagg accaggacgg cgccgggctc ggggtcggtc gggttcaggg cgatgccccg     660
ctcggtgcag agatccacga tcgggcgcgc gggcaccggg tcgacgatgg tggtgcggcg     720
cgggtcgagg cccgcgtcca gccagcccgc cagcatcgcg ccgcccatct tgccggcccc     780
ggccaggacc agggaggcgg gcatccgcgc cgtcgaggcg cccggccgg tcac           834

<210> SEQ ID NO 18
<211> LENGTH: 277
<212> TYPE: PRT
<213> ORGANISM: Methylobacterium radiotolerans

<400> SEQUENCE: 18

Met Thr Gly Pro Gly Ala Ser Thr Ala Arg Met Pro Ala Ser Leu Val
1               5                   10                  15

Leu Ala Gly Ala Gly Lys Met Gly Gly Ala Met Leu Ala Gly Trp Leu
```

```
                    20                  25                  30
Asp Ala Gly Leu Asp Pro Arg Arg Thr Thr Ile Val Asp Pro Val Pro
            35                  40                  45

Ala Arg Pro Ile Val Asp Leu Cys Thr Glu Arg Gly Ile Ala Leu Asn
50                  55                  60

Pro Thr Asp Pro Glu Pro Gly Ala Val Leu Val Leu Gly Ile Lys Pro
65                  70                  75                  80

Gln Gly Leu Asp Thr Ala Ala Pro Gly Leu Asp Arg Leu Ile Gly Arg
                85                  90                  95

Asp Thr Leu Leu Val Ser Ile Leu Ala Gly Lys Thr Val Ala Asp Leu
            100                 105                 110

Arg Gly Arg Leu Pro Arg Ala Arg Ala Ile Val Arg Ala Met Pro Asn
            115                 120                 125

Leu Pro Ala Ser Ile Gly Arg Gly Ala Thr Gly Ala Cys Ala Ser Pro
        130                 135                 140

Glu Val Thr Pro Ala Gln Arg Ala Ala Glu Ala Leu Leu Ala Ala
145                 150                 155                 160

Asn Gly Ala Val Ala Trp Leu Thr Asp Glu Ala Gln Ile Asp Ala Val
                165                 170                 175

Thr Ala Val Ser Gly Ser Gly Pro Ala Tyr Val Phe Leu Leu Ala Glu
            180                 185                 190

Thr Leu Ala Glu Ala Gly Ile Ala Ala Gly Leu Glu Pro Glu Val Ala
        195                 200                 205

Arg Ser Leu Ala Arg Ala Thr Val Ala Gly Ala Gly Ala Leu Leu Asp
        210                 215                 220

Ala Ser Pro Ala Glu Ala Ala Glu Leu Arg Arg Asn Val Thr Ser Pro
225                 230                 235                 240

Gly Gly Thr Thr Ala Ala Ala Leu Glu Val Leu Met Arg Pro Asp Gly
                245                 250                 255

Leu Gly Ala Leu Met Arg Glu Ala Val Ala Ala Arg Arg Arg Ala
            260                 265                 270

Gly Glu Leu Ser Gly
        275

<210> SEQ ID NO 19
<211> LENGTH: 819
<212> TYPE: DNA
<213> ORGANISM: Methylocystis sp.

<400> SEQUENCE: 19
gtgaccgacg cgggcgggct gcgcggaaag tcggtcgcgc tgatcggcgc cggaaacatg      60
gggctggcgt tgctcgaagg ctgggccgcg caagatttac tgggcgcagt gtcggtcgtc     120
gagccgcagc cgtcgcagcg gctccaggag ctgtgctccg cgcagggcta cgcgctgaac     180
ggcgcggctg ctccctgcga cgccgtggtt ctcgccgtta agccgcaggc gctgaggcg      240 ggcgccgcgc ggcggccccc tttcacggcg cgagacaccc tcgtcgtgtc gatcctcgcc     300
ggcaagcgcg ccgcggacgt cgccgcgcgc ctgccgacgc aagccgtggt gcgcgcaatg     360
ccaaatacgc cggcggcgat cgggcgcggc gtgaccggcg ccttcgccag cgcggcgacg     420
agcgcgcctc aacgcgtgtt ttccgatgca ttgctgagcg ccgtcggcgg cgtggaatgg     480
gtcgatgacg aggcgctcat cgacgtggtg acggcggttt ccggatcggg tccgcttat      540 gtcttctatt tcgccgaatg cctcgccgcc gccggcgccg aagccggtct gccggccgct     600
ctcgcggcgc ggctcgcccg cgcgacggtc gaaggcgccg cgagctgat gcgccggcag     660
```

| | |
|---|---|
| cccgagacag gccccgacga attgcgccgg cgcgtcactt cgccgggcgg cacgacggcg | 720 |
| gcggcgcttg aggttcttga ggcgccgac ggcctcgccg cactgatgcg ccgcgccgta | 780 |
| gctgcggcga agcgccgggc agggggaactt tccggttaa | 819 |

<210> SEQ ID NO 20
<211> LENGTH: 272
<212> TYPE: PRT
<213> ORGANISM: Methylocystis sp

<400> SEQUENCE: 20

```
Met Thr Asp Ala Gly Gly Leu Arg Gly Lys Ser Val Ala Leu Ile Gly
 1               5                   10                  15
Ala Gly Asn Met Gly Leu Ala Leu Leu Glu Gly Trp Ala Ala Gln Asp
                20                  25                  30
Leu Leu Gly Ala Val Ser Val Glu Pro Gln Pro Ser Gln Arg Leu
             35                  40                  45
Gln Glu Leu Cys Ser Ala Gln Gly Tyr Ala Leu Asn Gly Ala Ala Ala
         50                  55                  60
Pro Cys Asp Ala Val Leu Ala Val Lys Pro Gln Ala Leu Glu Ala
 65                  70                  75                  80
Gly Ala Ala Ala Ala Pro Phe Thr Ala Arg Asp Thr Val Val Val
                 85                  90                  95
Ser Ile Leu Ala Gly Lys Arg Ala Ala Asp Val Ala Ala Arg Leu Pro
                100                 105                 110
Thr Gln Ala Val Val Arg Ala Met Pro Asn Thr Pro Ala Ala Ile Gly
            115                 120                 125
Arg Gly Val Thr Gly Ala Phe Ala Ser Ala Ala Thr Ser Ala Pro Gln
        130                 135                 140
Arg Val Phe Ser Asp Ala Leu Leu Ser Ala Val Gly Gly Val Glu Trp
145                 150                 155                 160
Val Asp Asp Glu Ala Leu Ile Asp Val Val Thr Ala Val Ser Gly Ser
                165                 170                 175
Gly Pro Ala Tyr Val Phe Tyr Phe Ala Glu Cys Leu Ala Ala Ala Gly
            180                 185                 190
Ala Glu Ala Gly Leu Pro Ala Ala Leu Ala Arg Leu Ala Arg Ala
        195                 200                 205
Thr Val Glu Gly Ala Gly Glu Leu Met Arg Arg Gln Pro Glu Thr Gly
    210                 215                 220
Pro Asp Glu Leu Arg Arg Arg Val Thr Ser Pro Gly Gly Thr Thr Ala
225                 230                 235                 240
Ala Ala Leu Glu Val Leu Glu Ala Pro Asp Gly Leu Ala Ala Leu Met
                245                 250                 255
Arg Arg Ala Val Ala Ala Ala Lys Arg Arg Ala Gly Glu Leu Ser Gly
            260                 265                 270
```

<210> SEQ ID NO 21
<211> LENGTH: 822
<212> TYPE: DNA
<213> ORGANISM: Methylocella silvestris

<400> SEQUENCE: 21

| | |
|---|---|
| atgccggcgg tagcagcgtc tttcccagcc tcgctggtcc tggcgggcgc gggcaagatg | 60 |
| ggcggcgcga tgttgcgcgg ctggctcgac gcagggctcg acccggcgac tctcgccgtc | 120 |
| atcgatccca acgccggcgc ggatctcgcc agccttgcgg cggagcgcgg gttttctctg | 180 |

```
aatggcgctg cggcggcgcc tgaagttctg gtgctggcga tcaagccgca ggcgctcgac    240
gaggcgaccg cgctcgcggc gctcgcgacc cctcaaacgc tggtcatctc cattctggcg    300
ggcaagagca tcgccgacgt caaaaagcgg ctgcccggcg cgggcgcgat tgtccgcgcc    360
atgcccaatc taccggcttc ggtcgggcgc ggcatgaccg gctcaaagc cggggccggg    420 ctgaccgaaa cgcaaaagaa agcgaccgaa gccttgatcg gcgcgacggg cggcttcgaa    480
tgggtcgagg acgaaagact gatcgacgcc gtgacggcca tttccggctc cggccccgcc    540
tatgtgttct atctcgccga atgcctcgcc aaggccggcg aagcgctcgg cctttcgccg    600
ccggtcgccg cgcgcctcgc ccgggcgacg gtcgaagggg cgggcgaatt gctatttcaa    660
agcgccgata aaacgccggc gcaattgcgc gaaagcgtca cctcgccggg gggcaccacg    720
gccgcagcgc ttgaggtgct gatggccgcg gatgggctgg agccgctggc gcgccgcgcc    780
gccgaggccg cgcgccggcg cgcgcaggcg ctgtcaggct ag                       822
```

```
<210> SEQ ID NO 22
<211> LENGTH: 273
<212> TYPE: PRT
<213> ORGANISM: Methylocella silvestris

<400> SEQUENCE: 22

Met Pro Ala Val Ala Ala Ser Phe Pro Ala Ser Leu Val Leu Ala Gly
1               5                   10                  15

Ala Gly Lys Met Gly Gly Ala Met Leu Arg Gly Trp Leu Asp Ala Gly
            20                  25                  30

Leu Asp Pro Ala Thr Leu Ala Val Ile Asp Pro Asn Ala Gly Ala Asp
        35                  40                  45

Leu Ala Ser Leu Ala Ala Glu Arg Gly Phe Ser Leu Asn Gly Ala Ala
    50                  55                  60

Ala Ala Pro Glu Val Leu Val Leu Ala Ile Lys Pro Gln Ala Leu Asp
65                  70                  75                  80

Glu Ala Thr Ala Leu Ala Ala Leu Ala Thr Pro Gln Thr Leu Val Ile
                85                  90                  95

Ser Ile Leu Ala Gly Lys Ser Ile Ala Asp Val Lys Lys Arg Leu Pro
            100                 105                 110

Gly Ala Gly Ala Ile Val Arg Ala Met Pro Asn Leu Pro Ala Ser Val
        115                 120                 125

Gly Arg Gly Met Thr Gly Leu Lys Ala Gly Ala Gly Leu Thr Glu Thr
    130                 135                 140

Gln Lys Lys Ala Thr Glu Ala Leu Ile Gly Ala Thr Gly Gly Phe Glu
145                 150                 155                 160

Trp Val Glu Asp Glu Arg Leu Ile Asp Ala Val Thr Ala Ile Ser Gly
                165                 170                 175

Ser Gly Pro Ala Tyr Val Phe Tyr Leu Ala Glu Cys Leu Ala Lys Ala
            180                 185                 190

Gly Glu Ala Leu Gly Leu Ser Pro Val Ala Ala Arg Leu Ala Arg
        195                 200                 205

Ala Thr Val Glu Gly Ala Gly Glu Leu Leu Phe Gln Ser Ala Asp Lys
    210                 215                 220

Thr Pro Ala Gln Leu Arg Glu Ser Val Thr Ser Pro Gly Gly Thr Thr
225                 230                 235                 240

Ala Ala Ala Leu Glu Val Leu Met Ala Ala Asp Gly Leu Glu Pro Leu
                245                 250                 255
```

Ala Arg Arg Ala Ala Glu Ala Ala Arg Arg Ala Gln Ala Leu Ser
            260                 265                 270

Gly

<210> SEQ ID NO 23
<211> LENGTH: 819
<212> TYPE: DNA
<213> ORGANISM: Methylobacterium nodulans

<400> SEQUENCE: 23

```
tcaccccgac aattcggccg agcggctctt ggccgccgcc acggccgcgc gcagcaggtc    60
ggggaggccg cccgccgcca tcagcacgcc gagcgccgcc gcggtggtgc cgcccggcga   120
ggtcacgttc tggcgcagga tccccggttc gaggggcgctc tcggcgagga gcgcgcccgc   180
gcccgccacg gtctggcggg cgaggcgggc ggcgacatcc ggcggcaggc cggcggcggc   240
gccggcctcg gccagcgcct cggcgagcag gaacacatag gccgggccgg agccggagac   300
ggccgtcacg gcgtcgatca ggctctcgtc ggcgagccat ccacgaggc ctatccctga   360
gaggagcgcg tcggccatgc ggcgctggcg ctcgctcgtc tcggggctcg ccgccgcccc   420
ggtggcgccc cggccgatgc tggccggcag gttcggcatc gcccgcacca cggcccgggc   480
ctggggcagg cgggccttga ggttcgccac cgtcttgccc gccagcaccg agacgacgag   540
ggtgtcgggg cctacgagtg cgccaccgc ggaggaggcc gcctccagcc cctgcggctt   600
gatagccagc acgagcgcct cgggcggcgt caggccctcc gggttgaggg cgatgccgtg   660
gcgcccgcaa aggcggtga gatcgggcga ggccccggga tcgaccaccg cgatgcggga   720
cccgtcgagg ccgcccgcga gccagccctc cagcatggcg ccgcccatct tgccggcgcc   780
gacgaggacg agggaggcgg ggagatcgga ggcggtcat                         819
```

<210> SEQ ID NO 24
<211> LENGTH: 272
<212> TYPE: PRT
<213> ORGANISM: Methylobacterium nodulans

<400> SEQUENCE: 24

Met Thr Ala Ser Asp Leu Pro Ala Ser Leu Val Leu Val Gly Ala Gly
1               5                   10                  15

Lys Met Gly Gly Ala Met Leu Glu Gly Trp Leu Ala Gly Gly Leu Asp
            20                  25                  30

Gly Ser Arg Ile Ala Val Val Asp Pro Gly Ala Ser Pro Asp Leu Thr
        35                  40                  45

Ala Leu Cys Gly Arg His Gly Ile Ala Leu Asn Pro Glu Gly Leu Thr
    50                  55                  60

Pro Pro Glu Ala Leu Val Leu Ala Ile Lys Pro Gln Gly Leu Glu Ala
65                  70                  75                  80

Ala Ser Ser Ala Val Ala Pro Leu Val Gly Pro Asp Thr Leu Val Val
                85                  90                  95

Ser Val Leu Ala Gly Lys Thr Val Ala Asn Leu Lys Ala Arg Leu Pro
            100                 105                 110

Gln Ala Arg Ala Val Val Arg Ala Met Pro Asn Leu Pro Ala Ser Ile
        115                 120                 125

Gly Arg Gly Ala Thr Gly Ala Ala Ser Pro Glu Thr Ser Glu Arg
    130                 135                 140

Gln Arg Arg Met Ala Asp Ala Leu Leu Ser Gly Ile Gly Leu Val Glu
145                 150                 155                 160

```
Trp Leu Ala Asp Glu Ser Leu Ile Asp Ala Val Thr Ala Val Ser Gly
                165                 170                 175

Ser Gly Pro Ala Tyr Val Phe Leu Leu Ala Glu Ala Leu Ala Glu Ala
            180                 185                 190

Gly Ala Ala Ala Gly Leu Pro Pro Asp Val Ala Ala Arg Leu Ala Arg
        195                 200                 205

Gln Thr Val Ala Gly Ala Gly Ala Leu Leu Ala Glu Ser Pro Leu Glu
    210                 215                 220

Pro Gly Ile Leu Arg Gln Asn Val Thr Ser Pro Gly Gly Thr Thr Ala
225                 230                 235                 240

Ala Ala Leu Gly Val Leu Met Ala Ala Gly Gly Leu Pro Asp Leu Leu
                245                 250                 255

Arg Ala Ala Val Ala Ala Ala Lys Ser Arg Ser Ala Glu Leu Ser Gly
            260                 265                 270
```

<210> SEQ ID NO 25
<211> LENGTH: 822
<212> TYPE: DNA
<213> ORGANISM: Methylibium petroleiphilum

<400> SEQUENCE: 25

```
tcagccgccg aactcgtcgc ccagctcgac cgcgcggcgc tgcgccgcac gaacagcgcg      60
cacgatcgcc gccggcacgc cgtcggcctg catcgcgacg agcgccgcat gcgtggtgcc     120
gccgcgcgag gtgacgcgct cgcgcagcac cgacggcggc tcggcgctct cgccgccag     180
cgcggtggcg ccggagaagg tgccgagcgc cagcgcccgg ccctgctcgg cgtcaggcc     240
catgtcgcgc gcggcgtcca tcagcgcctc gatgaacagg aacacgtagg ccgggccgga     300
gcccgacagg gcggtcacgg cgtcgaggtc ggcctcgcga tcgacccaca gcgtggcgcc     360
ggtgggcgcc agcagcgcct cgacgctgct cgctggccg cgtcgacct cgggccgcgc      420
gtacagcccg gcaatgccct ggccgatcag cgcgggcgtg ttgggcatcg cccgcaccac     480
gcagcggttg ccggtggcgg cgacgatggc gtcggtgcgg atgcccgcca tgacgctgag     540
ctgggcggcc tcgcccacat gcggcgcgca gggcgcggcc gcctcccgga agatctgggg     600
cttcacggcc acaccacca ggccggcatc ggccagcgcc ggcgtcgcct gctcggtggc      660
gacgatgccg aaggcctgct tcaggcgctc gcgctgctcg gcccagggtt cgacgaccag     720
gacttcgtgc gcgtgcacgc cgctgcgcaa caggccgccg atcagcgcgc tggccatgtt     780
gccgccgccg atgaaggcga tgggagagga aggtggttc at                         822
```

<210> SEQ ID NO 26
<211> LENGTH: 273
<212> TYPE: PRT
<213> ORGANISM: Methylibium petroleiphilum

<400> SEQUENCE: 26

```
Met Asn His Leu Ser Ser Pro Ile Ala Phe Ile Gly Gly Gly Asn Met
1               5                   10                  15

Ala Ser Ala Leu Ile Gly Gly Leu Leu Arg Ser Gly Val His Ala His
            20                  25                  30

Glu Val Leu Val Val Glu Pro Trp Ala Glu Gln Arg Glu Arg Leu Lys
        35                  40                  45

Gln Ala Phe Gly Ile Val Ala Thr Glu Gln Ala Thr Pro Ala Leu Ala
    50                  55                  60

Asp Ala Gly Leu Val Val Trp Ala Val Lys Pro Gln Ile Phe Arg Glu
65                  70                  75                  80
```

```
Ala Ala Ala Pro Cys Ala Pro His Val Gly Glu Ala Ala Gln Leu Ser
                85                  90                  95

Val Met Ala Gly Ile Arg Thr Asp Ala Ile Val Ala Ala Thr Gly Asn
            100                 105                 110

Arg Cys Val Val Arg Ala Met Pro Asn Thr Pro Ala Leu Ile Gly Gln
        115                 120                 125

Gly Ile Ala Gly Leu Tyr Ala Arg Pro Glu Val Asp Ala Gly Gln Arg
    130                 135                 140

Ser Ser Val Glu Ala Leu Leu Ala Pro Thr Gly Ala Thr Leu Trp Val
145                 150                 155                 160

Asp Arg Glu Ala Asp Leu Asp Ala Val Thr Ala Leu Ser Gly Ser Gly
                165                 170                 175

Pro Ala Tyr Val Phe Leu Phe Ile Glu Ala Leu Met Asp Ala Ala Arg
            180                 185                 190

Asp Met Gly Leu Thr Pro Glu Gln Gly Arg Ala Leu Ala Leu Gly Thr
        195                 200                 205

Phe Ser Gly Ala Thr Ala Leu Ala Ala Gln Ser Ala Glu Pro Pro Ser
    210                 215                 220

Val Leu Arg Glu Arg Val Thr Ser Arg Gly Gly Thr Thr His Ala Ala
225                 230                 235                 240

Leu Val Ala Met Gln Ala Asp Gly Val Pro Ala Ala Ile Val Arg Ala
                245                 250                 255

Val Arg Ala Ala Gln Arg Arg Ala Val Glu Leu Gly Asp Glu Phe Gly
            260                 265                 270

Gly

<210> SEQ ID NO 27
<211> LENGTH: 36
<212> TYPE: DNA
<213> ORGANISM: Artificial Sequence
<220> FEATURE:
<223> OTHER INFORMATION: Primer sequence

<400> SEQUENCE: 27
tatattttag agacgatgcc gccgccattt tcatgc                              36

<210> SEQ ID NO 28
<211> LENGTH: 48
<212> TYPE: DNA
<213> ORGANISM: Artificial Sequence
<220> FEATURE:
<223> OTHER INFORMATION: Primer sequence

<400> SEQUENCE: 28
tgttcagtcg ggagaaaagg ggaagcgatg gacctgggct atctcgtc                 48

<210> SEQ ID NO 29
<211> LENGTH: 36
<212> TYPE: DNA
<213> ORGANISM: Artificial Sequence
<220> FEATURE:
<223> OTHER INFORMATION: Primer sequence

<400> SEQUENCE: 29
tatacccctg agacgggtac ggcagagaat ccgggc                              36

<210> SEQ ID NO 30
<211> LENGTH: 51
<212> TYPE: DNA
```

```
<213> ORGANISM: Artificial Sequence
<220> FEATURE:
<223> OTHER INFORMATION: Primer sequence

<400> SEQUENCE: 30
gacgagatag cccaggtcca tcgccccttt tctcccgact gaacaattcc g        51

<210> SEQ ID NO 31
<211> LENGTH: 20
<212> TYPE: DNA
<213> ORGANISM: Artificial Sequence
<220> FEATURE:
<223> OTHER INFORMATION: Primer sequence proC-F

<400> SEQUENCE: 31
ggtccgacca ttccagccgg                                            20

<210> SEQ ID NO 32
<211> LENGTH: 20
<212> TYPE: DNA
<213> ORGANISM: Artificial Sequence
<220> FEATURE:
<223> OTHER INFORMATION: Primer sequence

<400> SEQUENCE: 32
tcatcggcgg caacccagag                                            20

<210> SEQ ID NO 33
<211> LENGTH: 39
<212> TYPE: DNA
<213> ORGANISM: Artificial Sequence
<220> FEATURE:
<223> OTHER INFORMATION: Primer sequence

<400> SEQUENCE: 33
tttttatttt ttacatccat ggggcccggg ttagaaaaa                       39

<210> SEQ ID NO 34
<211> LENGTH: 40
<212> TYPE: DNA
<213> ORGANISM: Artificial Sequence
<220> FEATURE:
<223> OTHER INFORMATION: Primer sequence

<400> SEQUENCE: 34
cgcgggaact gggggcttga tcgtcttcga attcggggtt                      40

<210> SEQ ID NO 35
<211> LENGTH: 40
<212> TYPE: DNA
<213> ORGANISM: Artificial Sequence
<220> FEATURE:
<223> OTHER INFORMATION: Primer sequence

<400> SEQUENCE: 35
aaccccgaat tcgaagacga tcaagccccc agttcccgcg                      40

<210> SEQ ID NO 36
<211> LENGTH: 40
<212> TYPE: DNA
<213> ORGANISM: Artificial Sequence
<220> FEATURE:
<223> OTHER INFORMATION: Primer sequence

<400> SEQUENCE: 36 gttttctaa cccgggcccc atggatgtaa aaaataaaaa                       40
```

<210> SEQ ID NO 37
<211> LENGTH: 40
<212> TYPE: DNA
<213> ORGANISM: Artificial Sequence
<220> FEATURE:
<223> OTHER INFORMATION: Primer sequence

<400> SEQUENCE: 37
tttttatttt ttacatccat gctagcttac tgaccgcttt                         40

<210> SEQ ID NO 38
<211> LENGTH: 40
<212> TYPE: DNA
<213> ORGANISM: Artificial Sequence
<220> FEATURE:
<223> OTHER INFORMATION: Primer sequence

<400> SEQUENCE: 38
cgcgggaact gggggcttga gaattcgaag acgaaaaacc                         40

<210> SEQ ID NO 39
<211> LENGTH: 40
<212> TYPE: DNA
<213> ORGANISM: Artificial Sequence
<220> FEATURE:
<223> OTHER INFORMATION: Primer sequence

<400> SEQUENCE: 39 ggttttcgt cttcgaattc tcaagccccc agttcccgcg                          40

<210> SEQ ID NO 40
<211> LENGTH: 40
<212> TYPE: DNA
<213> ORGANISM: Artificial Sequence
<220> FEATURE:
<223> OTHER INFORMATION: Primer sequence

<400> SEQUENCE: 40
aaagcggtca gtaagctagc atggatgtaa aaataaaaa                          40

<210> SEQ ID NO 41
<211> LENGTH: 40
<212> TYPE: DNA
<213> ORGANISM: Artificial Sequence
<220> FEATURE:
<223> OTHER INFORMATION: Primer sequence

<400> SEQUENCE: 41
tttttatttt ttacatccat ggtaccaagc ttgaattcgg                         40

<210> SEQ ID NO 42
<211> LENGTH: 40
<212> TYPE: DNA
<213> ORGANISM: Artificial Sequence
<220> FEATURE:
<223> OTHER INFORMATION: Primer sequence

<400> SEQUENCE: 42
cgcgggaact gggggcttga ggtaccccat gggctagcga                         40

<210> SEQ ID NO 43
<211> LENGTH: 40
<212> TYPE: DNA
<213> ORGANISM: Artificial Sequence
<220> FEATURE:

```
<223> OTHER INFORMATION: Primer sequence

<400> SEQUENCE: 43
tcgctagccc atggggtacc tcaagccccc agttcccgcg                           40

<210> SEQ ID NO 44
<211> LENGTH: 40
<212> TYPE: DNA
<213> ORGANISM: Artificial Sequence
<220> FEATURE:
<223> OTHER INFORMATION: Primer sequence

<400> SEQUENCE: 44
ccgaattcaa gcttggtacc atggatgtaa aaaataaaaa                           40

<210> SEQ ID NO 45
<211> LENGTH: 33
<212> TYPE: DNA
<213> ORGANISM: Artificial Sequence
<220> FEATURE:
<223> OTHER INFORMATION: Primer sequence

<400> SEQUENCE: 45
tatatagagc tcgctggaag gactcgggat gcc                                  33

<210> SEQ ID NO 46
<211> LENGTH: 31
<212> TYPE: DNA
<213> ORGANISM: Artificial Sequence
<220> FEATURE:
<223> OTHER INFORMATION: Primer sequence

<400> SEQUENCE: 46
tatataggta cctcaagccc ccagttcccg c                                    31
```